(12) United States Patent
Jülich et al.

(10) Patent No.: US 6,726,911 B1
(45) Date of Patent: Apr. 27, 2004

(54) **BIOLOGICALLY ACTIVE COMPOUNDS OF *GANODERMA PFEIFFERI* DSM 13239**

(75) Inventors: Wolf Jülich, Greifswald (DE); Ulrike Lindequist, Greifswald (DE); Rolf Jansen, Braunschweig (DE); Ramzi Mothana, Greifswald (DE)

(73) Assignee: Ganomycin, Greifswald (DE)

( * ) Notice: Subject to any disclaimer, the term of this patent is extended or adjusted under 35 U.S.C. 154(b) by 0 days.

(21) Appl. No.: 09/936,167

(22) PCT Filed: Mar. 8, 2000

(86) PCT No.: PCT/EP00/02026
§ 371 (c)(1), (2), (4) Date: Dec. 10, 2001

(87) PCT Pub. No.: WO00/53207
PCT Pub. Date: Sep. 14, 2000

(30) Foreign Application Priority Data

Mar. 9, 1999 (DE) .......................... 199 11 680
Mar. 9, 1999 (DE) .......................... 199 11 679

(51) Int. Cl.$^7$ .............................. A61K 35/84
(52) U.S. Cl. .................................. 424/195.15
(58) Field of Search ..................... 424/195.15

(56) References Cited

U.S. PATENT DOCUMENTS 5,869,152 A    2/1999    Colon

FOREIGN PATENT DOCUMENTS

| EP | 0 591 603 A2 | 2/1993 |
|---|---|---|
| EP | 0 813 062 A2 | 12/1997 |
| WO | WO 97/17606 | 5/1997 |
| WO | WO 98/27418 | 6/1998 |

OTHER PUBLICATIONS

Schwarze et al. Eur J. Forest Pathol. 1995. vol. 25, No. 6–7, pp. 327–341.*

* cited by examiner

Primary Examiner—Christopher R. Tate
(74) Attorney, Agent, or Firm—Jacobson Holman PLLC

(57) ABSTRACT

The present invention relates to novel biologically active compounds from fungi of the species *Ganoderma pfeifferi* DSM 13239, processes for their preparation, and their use. From the fruit body and mycelium of the species *Ganoderma pfeifferi* DSM 13239, extracts can be obtained which have antimicrobial activity and are suitable as preserving agents, for pharmaceutical and cosmetic preparations, for controlling infections, and for use in fish breeding. Antimicrobially active substances called ganomycins having activity against multiresistant germs are isolated from the extracts. The total synthesis of the ganomycins and their derivatization enables their use an antibiotics.

19 Claims, No Drawings

BIOLOGICALLY ACTIVE COMPOUNDS OF *GANODERMA PFEIFFERI* DSM 13239

This is a 371 of PCT/EP00/02026, filed Mar. 8, 2000, the disclosure of which is incorporated herein by reference.

DESCRIPTION

The present invention relates to novel biologically active compounds from fungi of the species *Ganoderma pfeifferi* DSM 13239, processes for their preparation, and their use. From the fruit body and mycelium of the species *Ganoderma pfeifferi* DSM 13239, extracts can be obtained which have antimicrobial activity and are suitable as preserving agents, for pharmaceutical and cosmetic preparations, for controlling infections, and for use in fish breeding.

PRIOR ART

Biologically active compounds which can be obtained from certain fungi of the genus Ganoderma by extraction with solvents have long been described and summarized by us in a monograph (U. Lindequist: Ganoderma. In: Hagers Handbuch der pharmazeutischen Praxis/Ed. F. von Bruchhausen, 5th Edition, totally revised, Springer Publishers Berlin, Heidelberg, N.Y., 1998, Supplement Volume 2, Drogen A-K (Ed. W. Blaschek), pages 750–761. In the following, reference is made to the literature stated therein.

To date, commercially utilized drug-supplying species of the genus Ganoderma only include *Ganoderma applanatum* (*Ganoderma applanatum* fruit bodies) and *Ganoderma lucidum* (*Ganoderma lucidum* fruit bodies). Due to its valuable components, *G. lucidum* is grown commercially in various Asian countries (Japan, China, Korea etc.) in large amounts on artificial substrate (Hager, references 20, 25).

For extracting the active substances from *G. lucidum* and *G. applanatum*, various solvents have been employed. To date, dichloromethane and ethyl acetate have not been used.

The most important group of active substances of these fungi are the triterpenes, polysaccharides and sterols. More than 100 triterpenes have been structurally elucidated. They are referred to, inter alia, as ganoderic acids, ganodermic acids, ganoderenic acids, ganolucidic acids, ganosporeric acids, lucidenic acids, ganoderiols, epoxyganoderiols, ganoderals, ganoderols, lucidones, ganodermanonediol, ganodermanonetriol and ganodermatriol. Due to the different designations of a compound in different working groups, there are numerous double usages and unclarities. The basic body is a lanostane, which is mostly unsaturated, often with two conjugated double bonds in the ring system in positions 7 and 9(11), or one double bond in position 8 which is in conjugation with two oxo groups in positions 7 and 11. The acids have a carboxy group at the end of the side chain in position 26. In the trinortriterpenic acids (C27 compounds), the lucidenic acids, the carboxy group is in position 24. Methyl esters of the acids also exist. The hydroxy groups are in part acetylated or dehydrogenated into oxo groups. In some members, there has been degradation of the side chain to as few as two carbon atoms (C23 compounds).

During the development of the fruit bodies, changes in the triterpene pattern of the fungi occur. In the mycelium stage, the ganoderic acids are predominant, but with progressing development of the fruit bodies, lucidenic acids are increasingly occurring (Hager, reference 22). In the polysaccharides, a distinction can be made between glucanes, heteropolysaccharides and protein-bound polysaccharides.

In addition, various proteins, steroids, nucleotides and some further small-molecular compounds have been characterized in *Ganoderma lucidum*.

As the main sterols, ergosterol and ergosta-7,22-dienol have been identified (Hager, references 15, 56, 65). In addition, ergosterol peroxide, ergosta-7,22-diene-3β-yl palmitate (56, 66), 6α- and 6β-hydroxyergosta-4,7,22-triene-3-one (52), ergosta-7,22-diene-3β-yl linoleate, 5α,8α-epidioxyergosta-6,22-diene-3β-yl linoleate and ergosta-7,22-diene-2β-3α,9α-triol (66) have been identified.

Further components are adenosine in concentrations of from 40 mg/100 g of dried fruit bodies (Hager, reference 67), and 5'-deoxy-5'methylsulfinyladenosine (Hager, reference 68).

From extracts of the cultured mycelium, a polypeptide referred to as Ling Zhi-8 (LZ-8) and consisting of 110 amino acids and having a molecular weight of 12,420 Dalton has been isolated whose amino end is acetylated (Hager, references 69, 70). In addition, a lectin consisting of 2 protein subunits (molecular weights 55,600 and 59,800 Dalton) and a carbohydrate content of 2.56% has been found (Hager, reference 72).

Extracts from *G. lucidum* have long been used as medicaments. The effects of extracts from *Ganoderma lucidum* are very complex and varied, and it was seldom possible to date to assign them unambiguously to individual active substances. The following effects of extracts from *G. lucidum* belong to the prior art.

Extracts having effects on the CNS: An aqueous extract of the fruit bodies has centrally inhibiting and muscle-relaxing effects in mice. In a dose-dependent way, 30, 100 and 300 mg of the lyophilized extract per kg of body weight, s.c., suppress the activity of the animals in a running wheel, the locomotive activity and the centrally stimulating effect of caffeine. The pain threshold in the heat plate test is increased. In the tail pressing test, analgesic effects occur. 300 mg/kg prolongs the time until onset of death after the administration of strychnine (1.5 mg/kg, i.p.) or caffeine (400 mg/kg, i.p.), the spasms induced by the alkaloids not being influenced (Hager, reference 73). In rats, Ganoderma extracts are said to have a sleep-promoting effect (Hager, reference 74).

Extracts having effects on the cardiovascular system: Hexane and methanol extracts of the fruit bodies (1 mg/ml) significantly reduce the contraction rate of cultivated myocardial cells of mice in vitro by 25 and 80%, respectively. The hexane and aqueous extracts increase the contraction amplitude by about 15% at the mentioned concentration. Responsible compounds for the former effect are ganoderic acid S, ganoderal A and ganodermanonetriol. 0.1 mg/ml of this compound will result in a complete stop of the contractions. The increase of the amplitude is caused by ganoderic acid S, portensterol and ganodermanonetriol (Hager, reference 5).

In vivo, a lyophilized aqueous extract was administered to patients with essential hypertension (group I) and to patients with a mild or no hypertension (group II) orally in the form of tablets over a period of 6 months (6 tablets with 240 mg of extract per day). In the patients of group I, a significant decrease of the increased blood pressure occurred while that of patients of group II was not influenced. Side-effects did not occur (Hager, reference 76).

Spontaneously hypertensive rats whose feed contained 5% *Ganoderma lucidum* powder exhibited a significantly reduced systolic blood pressure and a reduced total cholesterol level in the plasma and liver as compared to the control group after 4 weeks with a corresponding diet (Hager, reference 77).

Morigiwa et al. (Hager, reference 39) found inhibition of the angiotensin-converting enzyme in 10 triterpenes in vitro and thus another possible explanation of the antihypertensive effects. The most potent was ganoderic acid F ($IC_{50}$ $4.7 \times 10^{-6}$ M). Ganoderal A, ganoderols A and B and the ganoderic acids B, D (C), H, K, S and Y were active with an average $IC_{50}$ of $10^{-5}$ M.

Extracts having effects on the blood: An aqueous extract (50 μl of the extract, 5 g of the fungus extracted with 300 ml) inhibits the thrombin-induced aggregation of bovine platelets in vitro. Adenosine has been identified as the responsible active substance (Hager, reference 67). On the other hand, raw extracts do not exhibit an anti-platelet activity in HIV-positive hemophilic patients despite of high adenosine concentrations (Hager, reference 78). Further active substances for which an effect on platelet aggregation has been detected in vitro include 5-deoxy-5-methylsulfinyladenosine (Hager, reference 79) and ganodermic acid S. In a concentration of 50 μg/ml, the adenosine derivate inhibits the ADP-induced aggregation of rabbit platelets, but not the PAF-stimulated aggregation (Hager, reference 79). Ganodermic acid S has membrane activity and influences the phosphoinositol metabolism in vitro. Depending on its concentration, it promotes or inhibits the aggregation of human platelets caused by different inductors in vitro (Hager, references 80, 81).

In an animal experiment, an aqueous extract (500 mg/kg) inhibits the decrease of platelet and fibrinogen levels and the prolongation of the prothrombin time in rats in which disseminated intravascular coagulations had been produced by the action of endotoxins. In vitro, this extract in concentrations of from 500 to 1000 μg/ml reduces the action of thrombin and the collagen-induced platelet aggregation (Hager, reference 82).

In addition, the influence of aqueous extracts on the aggregation of platelets from 15 healthy donors and 33 patients with arteriosclerosis was examined. In-vitro addition of the extract to the platelets of healthy subjects reduces aggregation in a concentration-dependent way. In vivo, the oral administration of 1 g of extract three times a day for 2 weeks to the patients results in a significant inhibition of ADP-induced platelet aggregation (Hager, reference 83).

Extracts having effects on the digestive tract: Some triterpenes (lucidenic acid A, lucidenic acid D1, ganoderic acid A, ganoderic acid C1, ganoderic acid J, lucidone A, lucidone C) have an intensive bitter taste and thus should have a digestion-stimulating and appetizing effect. The bitter taste of lucidenic acid D1 is still discernible in a dilution of $5 \times 10^{-10}$ (Hager, reference 84).

Extracts having effects on the liver: In vitro, a strong inhibition of the division of human hepatoma cells (PLC/PRF/5 cells) and of KB cells by ganoderaldehyde A ($ED_{50}$ for the hepatoma cells: 10.99 μg/ml; for KB cells: 9.75 μg/ml) and by ergosta-7,22-diene-2β,3α,9α-triol ($ED_{50}$ for the hepatoma cells: 1.17 mg/ml; for KB cells: 0.89 μg/ml) was achieved (Hager, reference 66).

The ganoderic acids T, U, V, W, X, Z also exhibit cytotoxic activity on hepatoma cells in vitro in doses of $10^{-4}$ mol (Hager, reference 47).

In contrast, the ganoderic acids R and S have an anti-hepatotoxic effect in vitro. They reduce the galactosamine-induced cytotoxicity in cultured rat hepatocytes (Hager, reference 45).

In rats, aqueous extracts of the fruit bodies (30 and 100 mg/kg, i.p.) reduce chloroform-induced liver toxicity (determination of GOT and LDH) (Hager, reference 85). In mice, alcoholic extracts antagonize the accumulation of lipid in the liver, which is also caused by chloroform. In addition, they reduce the mortality rate of the animals upon high doses of digitoxin and indomethacin. They promote the liver regeneration in partially hepatectomized animals (Hager, reference 6).

Two polysaccharide fractions obtainable from the mycelium by alkali treatment and ethanol precipitation (0.5 to 5 mg/rat/day for 4 weeks) exhibit antifibrotic effects in rats having experimentally induced hepatic cirrhosis (Hager, reference 87).

Extracts having effects on metabolism: Aqueous and ethanolic extracts of the fruit bodies were tested for their influence on the glucose and insulin levels in an oral glucose tolerance test in rats. The aqueous extract (50 mg/rat weighing 200–250 g) significantly reduced the glucose level in the blood after 10 min from an oral glucose administration as compared to the control rats. After 10 min, the insulin level was also reduced as compared to the control group, but 30 and 60 min after the glucose supply, it was on a significantly higher level as compared to the control group. In addition, the aqueous extract reduced the increase of the blood glucose level induced by i.v. administration of adrenalin and the adrenalin-induced lipolysis in rat adipocytes. The glucose absorption from the small intestine was not influenced. It is supposed that the effect of the aqueous extract is based on an improvement of glucose utilization in the peripheral tissue. The ethanolic extracts were hardly effective (Hager, reference 88).

Hikino et al. (Hager, references 62, 63, 89) found hypoglycemic effects in the polysaccharides referred to as ganoderanes. There is no overlap with the polysaccharides having antitumor activity (Hager, reference 90). The most active compound is ganoderane B. After 3 to 7 hours from the i.p. administration, 30 mg/kg of this compound significantly reduce the plasma glucose level in glucose-loaded mice. In normal animals, the effect is not so clearly pronounced. The hypoglycemic activity is attributed to an increase of the insulin concentration in the blood plasma and an enhancement of glucose metabolism (Hager, reference 63).

Other metabolic effects relate to the cholesterol level in the blood. Aqueous and alcoholic extracts of Ganoderma lucidum inhibit the cholesterol accumulation in cultured human aortic intimal cells and the proliferation of the cells. Therefore, antiarteriosclerotic properties of the fungus are assumed (Hager, reference 91).

Some oxygenated triterpenes having a carboxy group on C-26 (3α,15α-diacetoxy-5α-lanosta-7,9(11),24-triene-26-carboxylic acid, 3α,15α-dihydroxy-5α-lanosta-7,9(11),24-triene-26-onecarboxylic acid) are hardly absorbed in the gastro-intestinal tract of rats. In this way, much like sitosterol, they reduce the absorption of food-supplied cholesterol from the gastrointestinal tract and thus have a hypolipidemic effect (Hager, references 92, 93). Ganoderic acid derivatives changed by partial synthesis and having 7-oxo and 15α-hydroxy groups inhibit 14-demethylation during the biosynthesis of cholesterol from 24,25-dihydrolanosterol and are also said to be capable of reducing the cholesterol level in the blood (Hager, reference 94).

Extracts having effects on the immune system: Aqueous extracts of the fruit bodies exhibit antiallergic effects. In concentrations of from 20 to 500 μg/ml, they inhibit the release of histamine from peritoneal rat mast cells induced by the compound 48/80 (10 μg/ml) by 14 to 70% (95). In vivo, they reduce symptoms of experimental asthma in Guinea pigs (disorders of the respiratory rate and of the ratio of expiration/inspiration), of contact dermatitis induced by picryl chloride in mice (swelling of the ear), and of serum nephritis caused by immune complexes in rats (protein excretion, blood pressure, microscopic changes in the glomeruli). The dose administered p.o. was 500 mg/kg each (96).

The ganoderic acids C and D isolated from a methanolic extract of the fruit bodies, like the ethyl acetate phase of the starting extract, inhibit the release of histamine from peritoneal mast cells of rats induced by concanavaline A or the compound 48/80 in vitro. At 2 mg/ml, the mentioned compounds reduce the Con-A-induced release by 85% and $^{80}$%, respectively, and the 48/80-induced release by 70 and 80%, respectively (Hager, reference 31).

An extract exclusively prepared from the spores (water-soluble fraction of the ethanolic extract of the spores), in doses of 50, 100 and 200 mg/kg/day on 9 days i.p., inhibits the DTH response in mice induced by sheep erythrocytes, 2,4-dinitrochlorobenzene or allotypic splenocytes (Hager, reference 97).

The protein Ling Zhi-8 isolated from the mycelium has a mitogenic in vitro effect on T lymphocytes (Hager, reference 98). In doses of 6.9 mg/kg twice a week i.p., it inhibits the anaphylactic responses induced by bovine serum albumin in mice (99).

A chloroform extract from G. lucidum also exhibits an antiallergic effect (JP 0630 280 028 AA).

Extracts having anti-tumor activity: Extracts from G. lucidum and the ganoderic acids A-Z isolated therefrom exhibit anti-tumor activity (JP 0040304890 AA). Upon i.p. administration, a lyophilized hot-water extract of the fruit bodies alone or in combination with cytostatic agents (adriamycin, methotrexate and others) significantly prolongs the survival time of syngenic C57BL/6 mice into which a Lewis lung carcinoma had been grafted on an i.p. route. Pretreating the mice with cyclosporin inhibited this activity. Cytotoxicity could not be detected. Doses of 10 mg/kg i.p. on days 1, 3, 5, 7 and 9 after the tumor cell inoculation (day 0) prolonged the survival time by 95%. When combined with cytostatic agents, the effects were even more pronounced in part. The activity is attributed to a stimulation of the immune system by polysaccharides contained in the extract (Hager, reference 100). At a dosage of 10 mg/kg i.p. for 10 days, a hot-water extract of the fruit bodies reduces the weight of sarcoma 180 tumors in mice (ICR) by 99%. In one out of three animals, a complete regression occurred. The responsible fractions were those having a molecular weight of more than 10,000 Dalton. In contrast to aqueous extracts, methanolic extracts were not effective upon i.p. or p.o. administration (Hager, reference 101). The growth of a fibrosarcoma in C3H mice is also inhibited by aqueous extracts (Hager, references 102, 103).

Upon i.p. administration in doses of from 5 to 100 mg/kg, polysaccharide fractions obtainable from the fruit bodies by extraction with various solvents (hot water, 3% ammonium oxalate solution, 100° C., 5% NaOH, 30° C. and 80° C., etc.) reduce the growth of s.c. implanted sarcoma 180 tumors in ICR/JCL mice (Hager, references 57, 58, 59). Ten days of i.p. administration of 20 mg/kg of a water-soluble polysaccharide will inhibit the growth of solid sarcoma 180 tumors in mice by more than 90%. As the structure essential to this activity, a glucane with $\beta$1-3, $\beta$1-4, and $\beta$-1-6 linkages was identified (Hager, reference 102). In doses of 10 mg/kg/day i.p., a glucane fraction isolated in 1985 by Sone et al. resulted in complete regression of sarcoma 180 tumors in four out of five mice after 10 days. The anti-tumor activity is higher with the higher-branched glucanes (Hager, reference 61). A water-soluble polysaccharide fraction inhibited the tumor growth in BDF1 mice with leucemia P388 or L1210 and prolonged the survival time of the animals (Hager, reference 103).

Upon i.p. administration (20 mg/kg/day) to ICR mice, the polysaccharide-protein complex lucidane inhibits the growth of sarcoma 180 tumors by about 70% (64).

From the culture filtrate, an alkali-soluble glucane (1-3-linked glucose units with 1-2 and 1-6 branches) was extracted which inhibits the growth of sarcoma 180 tumors in mice by more than 90% upon i.p. administration in doses of 10 mg/kg/day on 10 days (Hager, reference 61).

After 5 days of repeated p.o. administration of polysaccharides to mice bearing sarcomas 180, a permanent increase of the phagocytosis index occurs (Hager, reference 105). The formation of oxygen radicals in isolated macrophages is stimulated (Hager, reference 103).

In a mixed lymphocyte culture, polysaccharides from Ganoderma lucidum extracts promote the IL-2 production 12 hours after initiation of the culture in a concentration-dependent way and enhance the regeneration of Lyt2+ and L3T4+ cells after 4 days (Hager, reference 107); other extracts have a scavenging effect on free radicals and thus exhibit anti-oxidative effects (Hager, references 85, 109) and cause a delay of ageing processes (Hager, references 60, 112). Promotion of the proliferation and differentiation of a human leucemic monocyte cell line (U 937) into mature monocytes/macrophages by 50 $\mu$g/ml of polysaccharides after 24 hours of incubation has been described (Hager, reference 111); doses of 25 and 50 mg/kg/day of a polysaccharide fraction i.p. for 4 days restore the activity of DNA polymerase $\alpha$ in 24-month-old mice to higher than the activity level of the enzyme in only 3-month-old animals. The reduced IL-2 production of splenocytes as compared to younger animals and the activity in the mixed lymphocyte culture are also increased again in the old animals to the levels of the young mice (Hager, reference 113).

Extracts containing ganoderic acids and obtainable by extraction from shake cultures of G. lucidum after transfer of the mycelium into a stationary culture have anti-tumor activity (JP 4-304890 AA). It has proven particularly advantageous to extract a particular fraction from G. lucidum with water and others with ethanol and to combine both extracts (JP 0600222423 AA).

Extracts having antimicrobial activity: In vitro, from 0.01 to 1 mg/ml of a methanolic raw extract inhibit the formation of plaque caused by the caryogenic bacteria Streptococcus mutans (S. Hada, M. Hattori, T. Namba, Pharmacology 113 (1990), 73. An extract obtainable from the pileus of Ganoderma lucidum inhibits the growth of staphylococci (DE 693 18 921 T2). It is state of the art to combine extracts from G. lucidum with antibiotics; however, the antimicrobial activity cannot be predicted since antagonism also frequently occurs (Chemical Abstracts Vol. 131, Nos. 182 146).

In a concentration of 20 $\mu$g/ml, a fraction of a methanolic extract from the fruit bodies referred to as F-III-4 and believed to contain ganoderic acids reduces the activity of reverse transcriptase in the culture supernatant of various HIV-infected cells by 40% and therefore deserves further interest as a potential anti-AIDS drug (Hager, reference 114). A triterpene obtainable by extraction from fungi of the Ganodermataceae, Polyporaceae or Lycoperdaceae families inhibits DNA polymerase (JP 0090-124690 AA).

Extracts having antiphlogistic activity: Aqueous extracts (2 g/kg, s.c.) exhibit a significant anti-inflammatory effect in the carrageen-induced ear edema of mice (Hager, reference 115). In the croton oil induced ear edema (mice), 500 µg/ear of the ethyl acetate extract, upon topical application and after 6 hours, is as effective as 200 µg/ear of hydrocortisone. Aqueous extracts (500 µg/ear) have not been effective here. Six hours after p.o. administration (1 hour before the topical administration of croton oil), 500 mg/kg of the ethyl acetate or aqueous extract had as strong an anti-inflammatory effect as 18 mg/kg of hydrocortisone. The effect of the Ganoderma extracts lasted longer (24 hours) than that of hydrocortisone (Hager, reference 23). The antimicrobial effect of *G. lucidum* extracts has been used for impregnating textiles (JP 0110060424 AA). Also from other Basidiomycetes, e.g., *Lentinus eodes*, hot-water extracts which exhibited activity against HIV became obtainable after autolysis (DE 689 06 245 T2).

Extracts having radioprotective activity: Continuous i.p. administration of an aqueous extract of *Ganoderma lucidum* to 6 to 7 weeks old male ICR mice before and after exposure of the animals to X-rays (500 and 650 cGy) reduced the deleterious effects of the radiation and increased the number of surviving animals (Hager, reference 116).

The occurrence of hydroquinones in fungi of the genus Ganoderma has not been known to date. Inter alia, hydroquinones form part of the respiratory chain and of photosynthesis and are therefore wide-spread in nature. The free-radical scavenging property of hydroquinones is pharmacologically interesting and is utilized in medicaments.

For the total synthesis of the active substances of the hydroquinone type isolated from Ganoderma, the following prior art can be considered: The synthesis of [2,5-bis[(tert.-butyldimethylsilyl)oxy]phenyl]acetaldehyde required as an intermediate is effected by starting from 2,5-dihydroxyphenethyl alcohol according to D. G. Hahngauer (Tetrahedron Lett., 1986, 27, 5799–5802).

The synthesis of the terpenoid side chains recurred to L. Chen, G. B. Gill, G. Pattenden, H. Simonian (J. Chem. Soc., Perkin Trans. 1, 1996, 31–44), F. Kido, Y. Noda, T. Maruyama, C. Kabuto, A. Yoshikoshi (J. Org. Chem., 1981, 46, 4264–4266), M. A. Avery, M. S. Verlander, M. Goodman (J. Org. Chem., 1980, 45, 2750–2753), E. J. Corey, M. A. Tius, J. Das (J. Amer. Chem. Soc., 1980, 102, 1742–1744), E. J. Corey, A. Venktateswarin (J. Amer. Chem. Soc., 1972, 94, 6190–6191), J. A. Marshall, D. G. Cleary (J. Org. Chem., 1986, 51, 858–863), T. R. Hoye, M. J. Kurth (J. Org. Chem., 1980, 45, 3549–3554), G. Beck, D. Gunther (Chem. Ber., 1973, 106, 2758–2766), and D. Grassi, V. Lippuner, M. Aebi, J. Brunner, A. Vasella (J. Amer. Chem. Soc., 1997, 119, 10992–10999).

The prior art further includes the oxidation of hydroquinones to quinones, which can be effected with various oxidants (W. M. Owton, J. Chem. Soc., Perkin Trans. 1, 1999, 2409–2420). Further, it is possible to employ 4-substituted phenols as a starting material. In the ruthenium-catalyzed oxidation with tert.-butyl hydro-peroxide in ethyl acetate, a rearrangement occurs to obtain 2-substituted quinones (W. M. Owton, J. Chem. Soc., Perkin Trans. 1, 1999, 2409–2420). Effectiveness against multiresistant bacteria has been known of none of the hydroquinones and quinones prepared to date by various methods. The same applies to conversion products of such hydroquinones and quinones known to date.

Mono- and dihydroquinone ethers are derived from hydroquinone by alkylation or arylation. In the medicine, hydroquinone benzyl ethers are employed against hyperpigmentations of the skin (liver spots, freckles) (Rompp Chemie-Lexikon, Georg Thieme Publishers Stuttgart, New York, 9th Edition, 1995). From the glucoside of hydroquinone, arbutin, which occurs, inter alia, in the leaves of *Arctostaphylos uva-ursi* (Ericaceae, bearberry), hydroquinone is released in the organism under certain conditions. The latter is held responsible for the urine-disinfecting activity of the drug (E. Teuscher, Biogene Arzneimittel, Wiss. Verlagsgesellschaft mbH, Stuttgart 1997). A coupling of active substances obtainable from Ganoderma species with other antibiotics has not been described to date. In principle, coupling reactions on antibiotics aiming at enhancing the effect by chemical conversions are known. Esterification of ofloxacin with ethanol is already known: J. S. Kiely, E. Laborde, L. E. Lesheski, R. A. Busch (J. Heterocycl. Chem., 1991, 28, 541–543).

Esterifications of penicillin G with simple alcohols also belong to the state of the art, e.g.: M. Murakami, M. Hajima, F. Takami, M. Yoshioka (Heterocycles, 1990, 31, 2055–264). The state of the art involves the use of enzymes to enable conversion under mild conditions.

The synthesis of cephalosporins is effected, for example, by the acylation of 7-aminocephalosporinic acid and 7-aminodeacetoxycephalosporinic acid by the catalytic action of acylases from *B. megaterium* or *E. coli* strains (T. Fujii, K. Hanamitsu, R. Izumi, T. Yamaguchi and T. Watanabe (1973), Japanese Patent 7399393, SNAM, Proetti (1972), Belgian Patent 782646). Lipases catalyze the esterification of a broad range of substrates (Ching et al., Angew. Chem. 101 (1989), 711–724). Therefore, the derivatization of new active substances from Ganoderma species can rely on these synthetic principles of the prior art in order to arrive at basically novel hybrid antibiotics.

The occurrence of *Ganoderma pfeifferi* as a tree fungus has long been known. However, no biologically active compounds trom the fungus *Ganoderma pfeifferi* have been known to date. Extracts from *G. pfeifferi* have not been reported in the literature, let alone employed as medicaments. The cultivation of *Ganoderma pfeifferi* in mushroom farms or in laboratory cultures has not been reported previously.

DRAWBACKS OF THE PRIOR ART

Although it could be expected that other Ganoderma species contain similar compounds as those isolated from *G. lucidum*, in contrast to the intensive medicinal utilization of *G. applanatum* and especially of *G. lucidum*, a utilization of other Ganoderma species and especially of *G. pfeifferi* has not been possible to date. Thus, the fungus is publicly accessible, but a commercial utilization of the wild fungi has not been effected previously. Thus, the valuable potential of this fungus has remained unused to date.

Antibiotics include substances produced by fungi and derivatives formed thereof which are able to control infections upon intrasomal application.

The components of *G. lucidum* and *G. applanatum* have not been used for the development of antibiotics although the antimicrobial activity of some extracts has been known. This is due to the fact that the various activities of the extracts from *G. lucidum* are very difficult to attribute to a specific active substance. It is just the wide variety of active substances from *G. lucidum* mentioned in the prior art which proves to be an obstacle to the development of an antibiotic because a substance having a dominant antimicrobial activity for which the recovery as an individual substance or the total synthesis appeared to be promising has not been isolated from *G. lucidum* and *G. applanatum*. The active substances isolated to date from *G. lucidum* or *G. applana-*

*tum* do not exhibit sufficient antimicrobial activity as individual substances. The extracts are difficult to standardize (JP 0610225649 AA), indefinite in their antimicrobial activity and therefore unsuitable as antibiotics.

However, the current state of the demands imposed on an antibiotic requires a well characterized active substance with defined pharmacokinetics and reproducible antimicrobial properties for the use as an antibiotic. To date, this precondition was not met by the materials recovered from *G. lucidum* or *G. applanatum*. Despite of the intensive search for active substances from fungi of the genus Ganoderma which can be used for pharmaceutical purposes, the isolation of compounds which are promising for the development of antibiotics due to their properties, the preparation of such active substances by chemical synthesis and derivatization have not been successful. Although a total synthesis of an active substance isolated from fungi is not indispensable to the development of an antibiotic, the preconditions for the development of an antibiotic are essentially improved by solving this problem.

Due to the increasing problems with resistances, there is still a high demand for antibiotics which is not satisfied by the extracts and active substances described in the prior art.

Especially in severe Gram-positive infections, only glycopeptide antibiotics are still sufficiently effective currently. However, staphylococci and enterococci are increasingly developing resistances against antibiotics from this group of substances, but also Gram-negative pathogens, for example, of the genus Pseudomonas, increasingly develop multiresistances so that infections with Gram-negative pathogens will no longer be safely controllable clinically in the future either. Also in veterinary medicine, infections of useful animals with multiresistant staphylococci become increasingly threatening. Additional danger is impending from a possible transfer to humans of pathogens having become resistant. In addition, the problem of infection control has been solved only unsatisfactorily to date in many other fields, e.g., in fish breeding. The increasing spread of breeding systems has led to great difficulties. Due to the ecological problems, only a few agents have been approved to date for treatment in fish-breeding systems. The problems cannot be solved with the active substances described in the prior art.

To overcome the problems of resistance in human and veterinary medicine, it is urgently necessary to develop new antibiotics. The object to be solved by the invention has been to make further Ganoderma species utilizable for medicinal use, to recover extracts therefrom, and to isolate active substances from such extracts and to further develop them by chemical conversions. In particular, it has been the object of the invention to meet the demand for new antibiotics due to the increasing development of bacterial resistances against conventional antibiotics, especially in the therapy of infectious diseases in human and veterinary medicine, by providing as yet unknown active substances from the genus Ganoderma and derivatives thereof.

To improve the preconditions for the development of an antibiotic, solutions should be found for also preparing the isolated active substances and products derived therefrom by chemical synthesis.

The object has been achieved by the recovery of as yet unknown active substances from naturally occurring fungi of the species *G. pfeifferi*, the culturing of *G. pfeifferi* DSM 13239 in mushroom farms, the culturing of *G. pfeifferi* DSM 13239 in fermenters, the preparation of different extracts from the cultured fungus, the isolation of antimicrobially active substances from these extracts, the preparation of these active substances by total synthesis, and the derivatization of these active substances.

The fungus of the species *G. pfeifferi* was deposited on Jan. 11, 2000, with the international deposit center DSMZ, Deutsche Sammlung von Mikroorganismen und Zelikulturen GmbH, Mascheroder Weg 1b, D-38124 Braunschweig, in accordance with the regulations of the Budapest Treaty. The deposit number is DSM 13239.

According to the invention, biologically active extracts from Ganoderma pfeifferi DSM 13239 can be obtained by treatment with solvents.

The extracts according to the invention can be obtained from both the fruit body of naturally occurring fungi of the species *Ganoderma pfeifferi* and the fruit bodies of fungi grown in mushroom farms.

The extracts can be advantageously obtained from the fruit body of the species Ganoderma pfeifferi DSM 13239 if the fungi are grown on wood substrates in mushroom farms. An as yet not realized technical solution for the medicinal utilization of the valuable components of *G. pfeifferi* is thereby achieved.

In a particularly advantageous way, the extracts can be obtained from the fruit body of the species *Ganoderma pfeifferi* DSM 13239 when the culturing of the fungi was performed after pretreating the wood with cellulose-degrading enzymes.

The extracts according to the invention can be obtained from the mycelium of the species *Ganoderma pfeifferi DSM* 13239 after growth in fermenters. Thus, another technical solution for the recovery of the components of Ganoderma species, especially *Ganoderma pfeifferi* DSM 13239, is achieved. Extracts obtainable from the mycelium of the species *Ganoderma pfeifferi* DSM 13239 after growth in fermenters are preferably employed since this opens a possibility for the recovery of biologically effective extracts and compounds which is independent of the tedious production of fruit bodies. It has proven advantageous to add ammonium succinate to the liquid medium. The extracts according to the invention can be obtained from the mycelium of the species *Ganoderma pfeifferi* DSM 13239 wherein the fungi are cultured in liquid media with carbohydrate sources, preferably in malt medium having a content of malt extract of from 20 to 40 g/1000 l and an initial pH of 4.5–7.5, with observance of a lighting and shaking regimen. In particular, it is advantageous to add wood extract, especially decoction from beech, alone or in combination with cellulose-degrading enzymes to the liquid medium.

From the fruit body and/or mycelium of the naturally occurring fungus or of the fungus grown by this method, extracts can be obtained with solvents of different polarities. Known extractants, such as cold and hot water, methanol, ethanol, acetone, ethyl ether, can be employed, but solvents which have not previously been employed in the extraction of Ganoderma species, such as dichloromethane and ethyl acetate, are particularly advantageous. Extracts according to the invention are advantageously obtained by extracting the fruit body or the mycelium with a lipophilic solvent, especially dichloromethane. Extracts according to the invention are also obtained by extracting the fruit body and/or the culture medium and/or the mycelium with ethyl acetate. Extracts obtainable by extraction with monohydric alcohols are recovered in particularly high yields. In this case too, the addition of wood decoction according to the invention is beneficial.

Also, it is in accordance with the invention to obtain extracts by water extraction, preferably at temperatures of from 10° C. to 80° C., wherein the extraction is advantageously effected stepwise with water of increasing temperature.

It is possible to perform the extraction in several steps with solvents having different polarities. Extracts according to the invention are obtained by extracting the residue obtained in the extraction with lipophilic solvents.

Extracts obtained by using monohydric alcohols for extracting the residue of dichloromethane extraction are advantageous.

Extracts obtained by using monohydric alcohols for extracting the residue of dichloromethane extraction can be further purified in a particularly advantageous way by partitioning with ethyl acetate and further purification on silica gel using gradients with the solvent dichloromethane/ethyl acetate 4:1 or on Sephadex. Extracts obtained by a water extraction of the residue of dichloromethane extraction and/or of the residue of ethanol extraction are also in accordance with the invention.

Extracts obtainable from the fruit bodies of naturally occurring fungi or of fungi grown in mushroom farms and from the mycelium of the species Ganoderma pfeifferi DKMS after growth in fermenters have proven to be biologically active. Surprisingly, ethanolic and aqueous extracts from the mycelium have a strong antiviral effect. With lipophilic extractants, extracts are obtained which exhibit effectiveness against Gram-positive bacteria. Monohydric alcohol extraction of the fruit bodies or mycelium of the strains of *G. pfeifferi* DSM 13239 grown according to the invention yields extracts which are effective against Gram-negative rod bacteria. Alcoholic extracts exhibit particular effectiveness against multiresistant bacteria of the genus Pseudomonas, which is not achieved with the dichloromethane extracts. Particularly active extracts are obtained by extracting with ethyl acetate the fruit body and/or the culture medium and/or the mycelium and/or the residue of extractions. Advantageously, the residue of extractions with monohydric alcohols can be employed. By another fractionation with a dichloromethane/ethyl acetate gradient, fractions having a high antimicrobial activity can be obtained.

It could not be predicted that an additional extract capable of inhibiting bacteria could be respectively obtained, for example, from the residue of dichloromethane extraction by ethanolic extraction, and from the residue of dichloromethane extraction and ethanolic extraction by a hot-water extraction.

In different fields of application, the extracts can be directly employed. It is also in accordance with the invention to use chromatographic methods for further processing the extracts obtainable from the fruit body or mycelium of strains of *G. pfeifferi* DSM 13239 cultured according to the invention, and to isolate pure active substances therefrom.

As expected, active substances known from *G. lucidum* or *G. applanatum*, such as ganoderol B, applanoxidinic acid G or triterpenes, can also be obtained thereby. Surprisingly, however, further active substances, such as the as yet unknown triterpene 3,26-dihydroxylanosta-8,24-diene-7-one, which we have called ganoderone B, can additionally be isolated. Triterpenes of the composition 3,26-dihydroxylanosta-8,24-diene-7-one can be obtained from the extracts of the fruit body and mycelium of *G. pfeifferi* DSM 13239 by extraction with solvent and have a remarkable biological activity. Ganoderone B has antiviral activity against influenza virus type A and inhibits the lipopolysaccharide binding to CD14+ cells.

Within the scope of the various pharmacological activities of the components of *G. lucidum* and *G. applanatum*, antibacterially active substances have as yet played an inferior role. Therefore, it could not be foreseen that, from the wide variety of possible extracts from *G. pfeifferi* DSM 13239, especially from the fruit body, there were prepared extracts having an antimicrobial activity which has a clearly superior activity as compared to that of extracts from *G. lucidum*. It was totally surprising that biologically active substances of general formula 1 can be obtained which have not previously been described either in other Ganoderma species or in other fungi, plants or animals. The compounds of general formula 1, referred to as ganomycins, are suitable as guiding structures for the development of antibiotics.

Active substances of formula 1 with residues R1–R5 can be obtained by the growth and extraction methods developed by us, wherein R1, R2 and R3 represent hydrogen, R5 represents $CH_3$ and $CH_2OH$, and R4 is in the form of a free acid; these active substances can also be obtained by chemical synthesis, which yields derivatives in which R1, R2 and R3 represent hydrogen, halogen, alkyl or alkoxy groups, R5 represents a —$CH_2$—aryl, —$CH_2$—alkyl, —$CH_2$-O-aryl, —$CH_2$—O-alkyl, —$CH_2N_3$, —$CH_2$-carboxylic acid, —$CH_2$-aldehyde or —$CH_2$-alcohol group, —$CH_2NR9_2$, —$CX_3$, —$CHX_2$, —$CH_2X$ or —$CH_3$, or bound to a carbohydrate derivative through a heteroatom, wherein X=F, Cl, Br, and R9 is a hydrogen atom, an alkyl or aryl residue, and R4 is selected to yield the free acid, an acid halide, amide, a salt or an ester with aliphatic or aromatic alcohols of the compound, and n is a number of from 1 to 10.

As stated in the Drawbacks of the Prior Art, it is a particular advantage to the development of an antibiotic when the natural substance found can also be prepared by a total synthesis.

Active substances which are provided with the following substituents in formula 1: R1, R2 and R3=H, F, Cl, Br, I or O-n-alkyl, R4=MeI, MeII, ammonium, alkylammonium, aryl or alkyl, R5=H, alkyl, aryl, R'OH, CHO, R'CHO, COOH or R'COOH (R'=aryl or alkyl); can be obtained by chemical synthesis by varying the synthetic route and the starting components.

According to the invention, this object was achieved by a variety of chemical processes.

By using substituted (2,5-dihydroxyphenyl) acetaldehydes, the found antimicrobially active basic structure can be further modified on positions R1 to R3. A particular amplification of activity is achieved by introducing halogens, especially fluorine, and of (2,5-dihydroxyphenyl)acetaldehydes substituted with methoxy groups on the ring system.

A process for the preparation of novel substituted hydroquinones and their derivatives is characterized in that the coupling of the hydroquinone substituted with residues R1–R3 to the terpenoid side chain is effected by starting from halogen-substituted hydroquinones via organometallic intermediates through the reaction with a terminal epoxide function of the terpenoid side chain.

It is also possible to effect the preparation of novel substituted hydroquinones and their derivatives in such a way that the coupling of the hydroquinone substituted with residues R1–R3 to the terpenoid side chain is effected by starting from halomethyl-substituted hydroquinones via organometallic intermediates through the reaction with a carbonyl function of the terpenoid side chain.

Another possibility for the preparation of novel substituted hydroquinones and their derivatives is characterized in that the coupling of the hydroquinone substituted with residues R1–R3 to the terpenoid side chain is effected by starting from substituted (2,5-dihydroxyphenyl) acetaldehydes through reaction with carbanions intermediately produced from suitable terpenoids.

The preparation of novel substituted hydroquinones and their derivatives may also be effected in such a way that the coupling of the hydroquinone substituted with residues R1–R3 to the terpenoid side chain is effected by starting from substituted 4-(2,5-dihydroxyphenyl)-2-methylidenecarboxylic acid esters bearing an electron-withdrawing leaving group in position 3 through reaction with carbanions intermediately produced from suitable terpenoids.

The process for the preparation of novel substituted hydroquinones and their derivatives is characterized by the stepwise deprotection of the synthesized compounds in order to obtain the free active substance or perform further functionalizations.

With different α-sulfonated carbonyl compounds, different side chains can be realized.

By alkylation or arylation of the active substances according to formula 1, mono-(formula 2) and dihydroquinone ethers (formula 3) can be obtained, wherein R6, R7 can be aryl, alkyl. These are also biologically active.

By introducing acid anhydrides as substituents on the carbon atom 18, biologically active compounds having a higher hydrophilicity are obtainable. Reaction with phthalic acid anhydride yields the active substance according to formula 4. By oxidation of the hydroquinones according to formula 1, the corresponding biologically active quinones (formula 5) can be obtained.

Active substances of general formula 1 can be linked by esterification to antibiotics bearing acid groups. On the one hand, this may be done on a chemical route using known reactions. The core of the present invention is the combination of new and known elements, whereby the choice of antimicrobially active compounds which are suitable for the treatment of infections with multiresistant germs is substantially enlarged. The wide variety of possible reactions for the active substances of formula 1 opens totally new routes in antibiotic therapy. According to the invention, it is particularly advantageous to effect the esterification by biotransformation. Novel antimicrobially active substances of formulas 5 to 12 and processes for their preparation are characterized in that active substances of general formula 1 are linked to antibiotics bearing amino groups through coupling at carbon atom 11. It is preferably to use active substances of general formula 1 with R4=CH$_3$ which are linked to antibiotics bearing amino groups through coupling at carbon atom 11, because the yields can be increased by 20% thereby.

By esterification of the hydroquinones of formula 1 (R5=CH$_2$OH), obtainable from *G. pfeifferi* DSM 13239 or prepared synthetically, with cis-1,2-epoxypropyl-phosphonic acid (fosfomycin), the active substance according to formula 6 can be obtained which will be bound particularly strongly to the surface of staphylococci through bonding to UDP N-acetyl-D-glucosaminyl-3-enol pyrovyl transferase. Thus, on the one hand, the synthesis of the bacterial cell wall is disturbed, and on the other hand, due to the particular properties of hydroquinone, the redox potential in the environment of the cell is influenced and the activity of extracellular enzymes is thus reduced.

Coupling the hydroquinones of formula 1 (R5=CH$_2$OH), obtainable from *G. pfeifferi* DSM 13239 or prepared synthetically, with the synthetically preparable inhibitor of cell wall synthesis, fosfonochlorine, yields an active substance of formula 7 which causes a particularly intense disturbance of the bacterial cell wall.

Binding the hydroquinones of formula 1 (R5=CH$_2$OH), obtainable from *G. pfeifferi* DSM 13239 or prepared synthetically, to liposidomycin yields an active substance of formula 8 which can be used to selectively influence the bacterial peptidoglucane synthesis.

Esterification of the hydroquinones of formula 1 (R5=CH$_2$OH), obtainable from *G. pfeifferi* DSM 13239 or prepared synthetically, with cephalosporin C results in an active substance of formula 9. The active substances of formula 10 obtained by reaction with β-lactam antibiotics inactivate the bacterial penicillinases and partially offset existing resistances. If the resistance occurred because the bacterial cell formed receptors having a particularly high affinity for penicillin, formation of the hydroquinones on the bacterial cell wall is achieved. Therefore, the hydroquinones can display their enzyme-inhibiting properties in immediate vicinity of the bacterial cell. Since Gram-positive bacteria rely on the activity of extracellular enzymes, an antibacterial effect is thus achieved.

By esterification of the hydroquinones of formula 1 (R5=CH$_2$OH), obtainable from *G. pfeifferi* DSM 13239 or prepared synthetically, with fusidinic acid, the active substance 11 can be obtained. This reaction causes an increase of surface activity and an enhancement of lipophilic properties.

Esterification of the active substances of formula 1, R5=CH$_2$OH, with ofloxacin results in active substance 12 by means of which an enlargement of the range of activities can be achieved.

Further novel antimicrobially active substances of formula 1 are obtained by binding to carbohydrate derivatives through a heteroatom at C18. The reaction of methyl-2,3,4-tri-O-benzyl-6-deoxy-6-iodo-β-D-glucopyranoside yields 11-(methyl-2,3,4-tri-O-benzyl-6-deoxy-β-D-glucopyranos-6-yl)oxy(2(1')Z,5E,9E)-2-[2'-(2,5-dihydroxyphenyl) ethylidene]-6,10-dimethyl-5,9-undecadienic acid which interacts with the bacterial cell membrane due to its carbohydrate moiety.

Therefore, it is possible to adapt the properties of the ganomycins of general formula 1 to the intended use by biotransformation and/or chemical derivatization.

The use of one or more of compounds of formula 1 and/or extracts according to Example 1 as free-radical scavengers is possible both in preservation technology and in various diseases. Also, the use of one or more of compounds of formula 1 and/or extracts according to claim 1 for inhibiting the activity of neutral endopeptidases and/or the angiotensin-converting enzyme is possible in various diseases because the proteases participate in numerous post-translational processes of the functional control of mammal organisms. By inhibiting these enzymes, anti-inflammatory, immunostimulant, analgetic, antihypertensive and antiviral activities have been achieved.

The use of one or more of compounds of formula 1 and/or extracts according to Example 1 for inhibiting the serum-mediated binding of lipopolysaccharides causes fever reduction and normalization of the distension of peripheral blood vessels in certain clinical pictures.

The use of biologically active extracts and/or compounds from fungi of the genus Ganoderma as substances and extracts having antimicrobial activity as a preservative for technical purposes, in particular, predominantly utilizes the antimicrobial properties.

The use of biologically active extracts and/or compounds from fungi of the genus Ganoderma as substances and extracts used as additives for pharmaceutical and cosmetic formulations, especially as preservatives, utilizes the favorable combination of antimicrobial activity, free-radical scavenging property, inhibition of proteases and the resulting anti-inflammatory effect.

The use of biologically active extracts and/or compounds from fungi of the genus Ganoderma as vitalizing and germ-reducing additives for foods, as food supplements and health-care agents also utilizes the combination of favorable properties and additionally causes relief of chronic pain.

The use of biologically active extracts and/or compounds from fungi of the genus Ganoderma for application in human and veterinary medicine, especially in the control of infections, as a sole active substance and in the form of combination preparations solves problems recently arisen in the control of multiresistant bacteria. In human medicine, the control of severe Gram-positive infections, which can be lethal as a consequence of sepsis, is becoming increasingly more difficult. Therefore, it is a particular advantage to be able to choose from a broad range of antimicrobially active compounds. The enlargement of the range of antimicrobially active substances by derivatizing the active substances according to formula 1 is therefore very important to provide agents having antimicrobial activity and different application properties for human and veterinary medicine. This applies, in particular, to a use with multiresistant Gram-positive germs. In veterinary medicine, staphylococcus infections play a great role mainly in the keeping of cattle because the germs are easily communicated during milking and can contaminate the milk. The application of the active substances of formula 1 can be done both systemically and locally.

The use as an agent against fish-pathogenic bacteria and in fish breeding results from the established activity against fish-pathogenic germs.

A particular advantage which results from the above properties is the use as agents with antimicrobial activity and as a free-radical scavenger. This use is characterized in that the extracts and the compounds isolated therefrom are used alone and in mutual combination. The established biological activities underlie the inventive application as a medicament containing one or more of the compounds and/or extracts. Formulations containing one or more of the compounds and/or extracts can be employed, in particular, for the preparation of a medicament for the treatment of Gram-positive infections and the sepsis caused by the infection. From the specific inhibiting activity of the extracts from *G. pfeifferi* DSM 13239 towards neutral endopeptidase, a use in the treatment of pain can be derived by interfering with the degradation of opinoid peptides and endorphins which act on the opiate receptors. On the other hand, inhibition of the neutral endopeptidase causes an inhibition of the degradation, suppression of aldosterone synthesis and enhancement of the renal sodium excretion. Thus, extracts from *G. pfeifferi* DSM 13239 can be employed in the treatment of hypertension. The use of one or more of the compounds and/or extracts obtainable from G. pfeifferi DSM 13239 for inhibiting the activity of neutral endopeptidases results in a substantial extension of the possible applications. Therefore, the use of one or more of the compounds and/or extracts according to the invention for the preparation of a medicament for the treatment of hypertension, cardiovascular diseases and metabolic disorders is possible.

The invention will be illustrated below by some Examples without being limited to these Examples.

EXAMPLES

Example 1

Comparative Examination of Extracts Obtainable From Ganoderma Species by Treatment With Solvents Methods: Fruit bodies of *G. pfeifferi* were collected on Fagus in Ludwigsburg (Mecklenburg-Western Pomerania), of G. lucidum on Quercus in Hamburg-Flottbeck, of *G. applanatum* on Fagus in Greifswald (Mecklenburg-Western Pomerania), and of *G. canosum* on Tsuga in Gorlitz (Saxony).

The freshly harvested fruit bodies were cleaned, cut into small pieces and dried in the air at room temperature, powdered in a beater mill and kept in a beater mill until used. Extracts of the fruit bodies were prepared and subjected to a comparative examination for biological activity.

In the first stage of examination, the agar diffusion test was employed. The extracts and substances to be tested were respectively dissolved using appropriate solvents (dichloromethane, methanol and water) and applied to filter paper sheets in different concentrations. Comparative sheets soaked with 25 $\mu$l of the corresponding solvent served as a control. Ampicillin (10 $\mu$g/sheet) was employed as a reference substance. The dried filter paper sheets were finally placed onto agar plates. For the basic screening, nutrient agar II (VEB Immunpraparate, Berlin, Germany) was employed, and for the examination on strains isolated from patient material, Mueller-Hinton II agar (Becton Dickinson Microbiology Systems, Cockeysville, USA) was employed. Using an inoculation wire loop, a pinheadful of test germ culture was suspended in 3 ml of a sterile 0.90% NaCl solution. Subsequently, 200 $\mu$l of the germ suspension was added to 20 ml of sterile, liquefied and slightly warm nutrient agar and cast into Petri dishes having a diameter of 10 cm. After placing the sheets onto the congealed agar, the plates were preincubated at 8° C. for about 2 to 3 hours, followed by incubation of the plates in an incubator at 37° C. for 24 hours. *Micrococcus flavus* was an exception. This culture was stored only at room temperature because the germ reaches its optimum growth at 20° C. The The evaluation of the plates was effected by measuring the diameters of the inhibition halos. All operations were done under aseptic conditions.

Results: In the comparative examination, extracts with solvents of different polarity obtainable from *G. pfeifferi* exhibit a clearly higher activity as compared to the extracts from other Ganoderma species (Tables 1–4).

TABLE 1

Comparison of the antibacterial activities of dichloromethane extracts

| | Diameter of inhibition halo in mm | | | |
|---|---|---|---|---|
| Test germ | G. pfeifferi | G. lucidum | G. applanatum | G. carnosum |
| S. aureus | 26 | 11 | 14 | 13 |
| B. subtilis | 21 | 11 | 13 | 12 |
| M. flavus | 30 | 13 | 14 | 13 |
| E. coli | 10 | —[1] | — | — |
| P. mirabilis | 18 | — | — | — |
| S. marcescens | 22 | — | — | — |

[1]no antibacterial activity

TABLE 2

Comparison of the antibacterial activities of ethanolic extracts

| | Diameter of inhibition halo in mm | | | |
|---|---|---|---|---|
| Test germ | G. pfeifferi | G. lucidum | G. applanatum | G. carnosum |
| S. aureus | 24 | 12 | —[1] | 16 |
| B. subtilis | 15 | 11 | — | 14 |
| M. flavus | 18 | 14 | — | 17 |
| E. coli | 8 | — | — | — |
| P. mirabilis | 17 | — | — | — |
| S. marcescens | 22 | — | — | — |

[1] no antibacterial activity

TABLE 3

Comparison of the antibacterial activities of cold-water extracts

| | Diameter of inhibition halo in mm | | | |
|---|---|---|---|---|
| Test germ | G. pfeifferi | G. lucidum | G. applanatum | G. carnosum |
| S. aureus | 12 | — | — | — |
| B. subtilis | — | — | — | — |
| M. flavus | 8 | — | — | — |
| E. coli | — | — | — | — |
| P. mirabilis | 9 | — | — | — |
| S. marcescens | — | — | — | — |

TABLE 4

Comparison of the antibacterial activities of hot-water extracts

| | Diameter of inhibition halo in mm | | | |
|---|---|---|---|---|
| Test germ | G. pfeifferi | G. lucidum | G. applanatum | G. carnosum |
| S. aureus | 32 | 16 | 17 | 10 |
| B. subtilis | 16 | 14 | 15 | 13 |
| M. flavus | 18 | 17 | 17 | 12 |
| E. coli | 12 | — | — | — |
| P. mirabilis | 25 | — | 11 | — |
| S. marcescens | 25 | — | — | — |

Example 2
Extracts Obtainable From the Fruit Body of the Species *Ganoderma pfeifferi* DSM 13239

Methods: Powdered fruit bodies were filled into extraction thimbles and extracted with dichloromethane (E. Merck, Darmstadt) in a Soxhlet apparatus to complete decoloration, which usually occurred after 24 h. After evaporating residual dichloromethane, the fungal residue was extracted five times for 2 h each with 80% ethanol (E. Merck, Darmstadt) with constant shaking at room temperature. The fungal residue was separated off using a Buchner funnel and dried in the air. Then, it was shaken five times for 2 h each with distilled water at room temperature, and the fungal residue was again separated off using a Büchner funnel. The residue of the cold-water extract was extracted three times with distilled water at 70° C. and subsequently filtered.

All extracts were concentrated in a vacuum rotary evaporator (Büchi Labortechnik AG, Flawil, Switzerland) at 40° C. and then lyophilized (Gefriertrocknungsanlagen GmbH, Osterode, Germany). In this form, they were available for extensive tests for biological activity, described in the following Examples.

Result: By extraction with solvents of different polarities, storable biologically active extracts can be obtained from the fruit body of *G. pfeifferi*.

Example 3
Extracts Obtainable From the Fruit Body of the Species *Ganoderma pfeifferi* DSM 13239, the Fungi Being Cultured in Mushroom Farms on Wood Substrates Methods: From freshly harvested young fruit bodies of the species *G. pfeifferi*, pieces of tissue were removed from the transitional region between the pileus and the stem using sterile forceps, and cultured at room temperature on Hagem agar. After the fungus showed visible growth, some pieces of mycelium were punched out and transferred into a Hagem liquid medium for 2–3 weeks. The media were prepared according to the protocols of Kreisel and Schauer (Methoden des mykologischen Laboratoriums, Fischer-Verlag, Jena 1987). With the mycelium obtained in this way, sterilized beechwood chips were infected as the substrate. After a culture time of 8 months at from 20 to 23° C. in suitable containers, the first fruit bodies could be recovered. The fruit bodies were processed and examined for biological activity according to Example 2.

Result: It is possible to culture the fruit bodies of *G. pfeifferi* on a suitable wood substrate. From the fruit bodies obtainable in this way, biologically active extracts can be obtained.

Example 4
Extracts Obtainable From the Fruit Body of the Species *Ganoderma pfeifferi* DSM 13239, the Culturing of the Fungi Being Effected Aafter Pretreatment of the Wood With Cellulose-degrading Enzymes Methods: Beech chips were incubated with a mixture of cellulose-degrading enzymes (Affina GmbH Berlin, Germany) for 24 h, followed by inoculation with *G. pfeifferi* by analogy with Example 3.

Result: The difficult step of initial growth in the substrate is improved by the pretreatment with cellulose-degrading enzymes. This provides a technical solution which facilitates the culturing of fungi which are difficult to induce to initial growth. The biological activity of the extracts is not influenced by the pretreatment.

Example 5
Extracts Obtainable From the Mycelium of the Species *Ganoderma pfeifferi* DSM 13239 After Initial Growth in Fermenters Methods: Freshly harvested young fruit bodies of the species *G. pfeifferi* were cleaned and broken up under sterile conditions. From the transitional region between the pileus and stem, pieces of tissue were removed using sterile forceps, and cultured at room temperature on Hagem agar. After the fungus showed visible growth, some pieces of mycelium were punched out and comminuted with a Hagem liquid medium in a Buhler homogenizer (Edmund Bühler, Tubingen, Germany). The further culture was then performed in 250 ml Erlenmeyer flasks with Hagem liquid medium according to H. Kreisel and F. Schauer (Methoden des mykologischen Laboratoriums, Fischer-Verlag, Jena 1987). To 100 ml each of culture medium was added 10 ml of the inoculating suspension prepared as described above. The culturing was effected at room temperature and under constant light conditions for 30 days, continuous mixing being achieved by means of a shaking machine (Innova 2100, New Brunswick Scientific Co., Inc. Edison, N.J., USA) at a rate of 125 rpm. Further scaling-up was effected by a transfer into a bioreactor having a volume of 10 l. To the fermenter was added 6 l of autoclaved HAGEM medium (liquid), followed by the addition of 60 ml of inoculating suspension. The culturing in the fermenter was effected at room temperature with constant aeration with sterile air and continuous stirring in a day-night cycle.

To determine the dry weight of the mycelium, the mycelium was separated from the medium by filtration, transferred to weighed crystallizing dishes, lyophilized by analogy with Example 2, and the dry weight was determined on a precision balance (Sartorius, Göttingen, Germany). The dried mycelia were filled into extraction thimbles and extracted with dichloromethane (E. Merck, Darmstadt) in a Soxhlet apparatus for 24 h. After the residual dichloromethane had evaporated, the mycelium residue was extracted three times for 2 h each with 80% ethanol (E. Merck, Darmstadt) with constant shaking at room temperature. The mycelium residue was separated off with a Buchner funnel and dried in the air. Then, it was shaken three times for 2 h each with distilled water at room temperature, and the fungal residue was again separated off using a Buchner funnel. The residue of the cold-water extract was extracted three times with distilled water at 70° C. and subsequently filtered.

All extracts were concentrated in a vacuum rotary evaporator (Büchi Labortechnik AG, Flawil, Switzerland) at 40° C. and then lyophilized (Gefriertrocknungsanlagen GmbH, Osterode, Germany). In this form, they were available for extensive tests for biological activity, described in the following Examples.

Result: The culturing of *G. pfeifferi* can be performed with liquid medium. Culturing in a 10 l fermenter permits the recovery of mycelium in larger amounts.

The average recovery is 5 g of mycelium per liter. The cultured fungus was deposited under the number DSM 13239 with the Deutsche Sammlung von Mikro-organismen und Zellkulturen GmbH, Mascheroder Weg 1b, D-38124 Braunschweig.

Example 6

Improvement of the Culturing Conditions by the Addition of Ammonium Succinate, Preferably in Concentrations of 0.1 to 1%

Methods: The experiments were performed according to Example 5, but with the addition of 0.1–1% ammonium succinate.

Result: Increase of the mycelium recovery from 0.34+0.0568 g/100 ml to 0.691+0.048 g/100 ml by the addition of 0.5% ammonium succinate.

Example 7

Extracts Obtainable From the Mycelium of the Species *Ganoderma pfeifferi* DSM 13239, the Fungi Being Cultured in Liquid Media With Carbohydrate Sources With Observance of a Lighting and Shaking Regimen.

Methods: Hagem medium, malt medium and a synthetic medium were examined for their suitability with special additions of trace elements and vitamins with observance of different lighting and shaking regimens using the methods stated in Example 5.

Result: Various liquid media are suitable for the culturing of *G. pfeifferi*. Preferably, malt medium having a content of malt extract of from 20 to 40 g/1000 l and an initial pH of 4.5–7.5 should be employed. Under such conditions, an increase of the mycelium weight from 0.061+0.0006 g/100 ml to 0.691+0.0482 g/100 ml is achieved during 30 days of culture. When a malt medium of pH 4.5 was used, yields of the dichloromethane extract of $1^5$% were achieved, which was significantly above the values of 1 to 7% which could be achieved under different culture conditions.

Example 8

Improvement of the Recovery of Mycelium and Extracts by the Addition of Wood Extract, Especially Decoction From Beech, Alone or in Combination With Cellulose-degrading Enzymes, to the Liquid Medium Methods: Wood decoction was prepared by 1 hour of cooking of 30 9 of comminuted wood of a beech with 300 ml of distilled water. The decoction was added to the culture batches according to Example 6 in a concentration of 10%. In part of the experiments, a mixture of cellulose-degrading enzymes (Affina GmbH, Berlin, Germany) was simultaneously added.

Result: The optimization of the culturing conditions causes an increase of the mycelium growth (control according to Example 6: 0.34+0.0568 g; optimized medium with wood extract addition: 1.079+0.1097 g/100 ml; optimized medium with wood decoction+cellulases: 1.481+0.12 g/100 ml), and an enhanced formation of secondary metabolites. After a culturing time of 30 and upon extraction with dichloromethane, the extract yield according to Example 6 was 30 mg, which was increased to 119 mg by the optimization, and the yield upon extraction with ethanol increased from 191 mg to 491 mg.

Example 9

Extracts Obtained by Extraction of the Fruit Body or Mycelium With a Lipophilic Solvent Methods: Powdered fruit bodies or lyophilized mycelium was filled into extraction thimbles and extracted with different lipophilic solvents in a Soxhlet apparatus for 24 h. All extracts were concentrated in a vacuum rotary evaporator (Büchi Labortechnik AG, Flawil, Switzerland) at 40° C., lyophilized (Gefriertrocknungsanlagen GmbH, Osterode, Germany), and then the dry weight was established.

Result: Dichloromethane is most suitable for obtaining a high yield of biologically active extracts.

Example 10

Extracts Obtained by Extraction of the Culture Medium With Ethyl Acetate

Methods: The medium of the fungal culture was concentrated to about 50 ml in a vacuum rotation evaporator (Büchi Labortechnik AG, Flawil, Switzerland) and then extracted by repeatedly shaking with ethyl acetate. The process was repeated until the ethyl acetate phase was no longer colored.

Result: Yields of between 0.1 and 0.5% were obtained. In an agar diffusion test according to Example 1, the extracts showed an inhibitory effect against *S. aureus* with inhibition halos of up to 17 mm.

Example 11

Extracts Obtainable by Extraction of Cultured Mycelium With Lipophilic Solvents, Preferably Dichloromethane Methods: In contrast to Example 9, the culture was harvested already after 5 days. The extraction was effected according to Example 9, and the determination of the antibacterial activity was effected according to Example 1 against *S. aureus* and *M. flavus*.

Result: Already after 5 days of culture, an antibacterial activity can be established by inhibition halos of 18 and 10 mm, respectively (Table 5).

TABLE 5

Antibacterial activity of dichloromethane extracts obtainable from cultures of *G. pfeifferi* after 5 days of culture

| Test germ | Inhibition halo (mm) |
|---|---|
| S. aureus | 18 |
| M. flavus | 20 |

Example 12
Extracts Obtainable by Extracting With Ethanol the Residue Obtained by the Extraction of Fruit Bodies of *G. pfeifferi* With Lipophilic Solvents Methods: The residue obtained by the extraction of *G. pfeifferi* with lipophilic solvents according to Example 9 was extracted five times for 2 h each with 80% ethanol (E. Merck, Darmstadt) with constant shaking at room temperature. The extract was separated off by filtration with a Büchner funnel and dried in the air. The test for antimicrobial activity was performed according to Example 1.

Result: The ethanolic extracts have antibacterial activity (Table 6).

TABLE 6

Antibacterial activity of ethanolic extracts from residues of the extraction according to Example 9

| Germ | Diameter of inhibition halo (mm) |
|---|---|
| S. aureus | 24 |
| B. subtilis | 15 |
| M. flavus | 18 |
| E. coli | 8 |
| P. mirabilis | 17 |
| S. marcescens | 22 |

Example 13
Extracts Obtainable by Water Extraction of the Residue From Dichloromethane Extraction Methods: The residue obtained by the extraction of *G. pfeifferi* with lipophilic solvents according to Example 9 was extracted five times for 2 h each with hot water of 70° C. with constant shaking at room temperature. The extract was separated off by filtration with a Büchner funnel and dried in the air. The test for antimicrobial activity was performed according to Example 1.

Result: The aqueous extracts have antibacterial activity (Table 7).

TABLE 7

Antibacterial activity of aqueous extracts from *G. pfeifferi*

| Germ | Diameter of inhibition halo (mm) |
|---|---|
| S. aureus | 32 |
| B. subtilis | 19 |
| M. flavus | 20 |
| E. coli | 12 |
| P. mirabilis | 26 |
| S. marcescens | 25 |

Example 14
Extracts Obtainable by Water Extraction of the Residue From Ethanol Extraction According to Example 12

Methods: The residue obtained by successive extractions of *G. pfeifferi* with lipophilic solvents and alcohols was extracted five times for 2 h each with hot water of 70° C. with constant shaking at room temperature. The extract was separated off by filtration with a Buchner funnel and dried in the air. The test for antimicrobial activity was performed according to Example 1.

Result: The aqueous extracts of the residue from ethanol extraction have antibacterial activity (Table 8).

TABLE 8

Antibacterial activity of aqueous extracts from residues of the extraction according to Example 12

| Germ | Diameter of inhibition halo (mm) |
|---|---|
| S. aureus | 32 |
| B. subtilis | 16 |
| M. flavus | 18 |
| E. coli | 12 |
| P. mirabilis | 25 |
| S. marcescens | 25 |

Example 15
Extracts From *G. pfeifferi* Cultured Mycelia Obtained by Extraction With Monohydric Alcohols Cultures of *G. pfeifferi* according to Example 7, in part with addition of wood decoction according to Example 8, were harvested on the 5th day of the experiment. The fungal mycelium was extracted five times for 2 h each with 80% ethanol (E. Merck, Darmstadt) with constant shaking at room temperature. The mycelium residue was separated off with a Buchner funnel. The extracts were concentrated in a vacuum rotary evaporator (Buchi Labortechnik AG, Flawil, Switzerland) at 40° C. and then lyophilized (Gefriertrocknungsanlagen GmbH, Osterode, Germany).

Result: By extraction with alcohols, extract yields can be obtained which amount to about one third of the total mycelium mass (Table 9).

TABLE 9

Extract yields and percentage of the total mass of the mycelium after 5 days of culturing

| Culturing conditions | Yield of ethanolic extract (mg) | Percentage of total mycelium mass |
|---|---|---|
| Malt medium, pH 5 | 549 | 32.5 |
| Malt medium, pH 7.5 | 596 | 30.3 |
| Malt medium, pH 5.5, with addition of beech decoction | 1308 | 35.9 |

Example 16

Extraction of Fruit Bodies and Cultured Mycelium With Water

Methods: Fruit bodies according to Example 1 and cultured mycelium according to Example 5 were extracted with water of 70° C. and, in a further experiment, first with water of 20° C. and subsequently with water of 70° C.

Results: Extracts are obtained which amount to about 6% of the mycelium total mass. A separation of the extracts is achieved when the extraction is performed in stages (Table 10).

TABLE 10

Yields of aqueous extracts and percentage of the total mass of the fruit body or mycelium

| Starting material/conditions | Yield of extract (mg) | Percentage of total mycelium mass |
|---|---|---|
| Fruit bodies, 70° C. | 45 | 7.5 |
| Mycelium, 70° C. | 42 | 7.0 |
| Fruit bodies, 20' C. | 27 | 4.5 |
| Mycelium, 20° C. | 28 | 4.7 |
| Fruit bodies, first 20° C., then 70° C. | 19 | 3.2 |
| Mycelium, first 20° C., then 70° C. | 14 | 2.4 |

Example 17
Extracts From Residues of the Extraction According to Example 9 Obtained by Extraction With Monohydric Alcohols Residues of an extraction according to Example 9 obtained from fungal cultures in synthetic medium and in malt medium, harvested on the 15th day of the experiment, were extracted five times for 2 h each with $^{80}\%$ ethanol (E. Merck, Darmstadt) with constant shaking at room temperature. The mycelium residue was then separated off with a Büchner funnel. The extracts were concentrated in a vacuum rotary evaporator (Büchi Labortechnik AG, Flawil, Switzerland) at 40° C. and then lyophilized (Gefriertrocknungsanlagen GmbH, Osterode, Germany).

Results: High yields of the ethanolic extracts are obtained (Table 11).

TABLE 11

Extract yields and percentage of the total mass of the mycelium after 15 days of curing

| Culturing conditions | Yield of ethanolic extract (mg) | Percentage of total mycelium mass |
|---|---|---|
| Synthetic medium, pH 5.5 | 274 | 38.5 |
| Malt medium, pH 5.5 | 756 | 20.9 |

Example 18
Extracts Obtainable From Residues of the Extraction According to Example 9

Methods: The residue remaining after the extraction of the fruit bodies with dichloromethane according to Example 9 was extracted with ethanol according to Example 17. The ethanolic extract was subsequently partitioned between water and ethyl acetate.

Result: The ethyl acetate phase has antimicrobial activity (Table 12).

TABLE 12

Antibacterial activity of the ethyl acetate extract

| Germ | Diameter of the inhibition halo |
|---|---|
| S. aureus | 16 mm |
| B. subtilis | 14 mm |
| M. flavus | 15 mm |

Example 19
Separation of the Extracts According to Example 18 Into Biologically Active Fractions Using Silica Gel Methods: The ethyl acetate phase according to Example 18 was fractionated through silica gel. A gradient of dichloromethane/ethyl acetate was used as the solvent, the further fractionation being performed with the gradient ethyl acetate/methanol.

Result: A large number of fractions were obtained all of which have antibacterial activity. Particularly active is the extract obtained with the solvent dichloromethane/ethyl acetate 4:1 (Table 13).

| Fraction | Activity against S. aureus (inhibition halo in mm) |
|---|---|
| Dichloromethane:ethyl acetate = 1:0 | 10 |
| Dichloromethane:ethyl acetate = 4:1 | 25 |
| Dichloromethane:ethyl acetate = 2:1 | 10 |
| Dichloromethane:ethyl acetate = 1:1 | 15 |
| Dichloromethane:ethyl acetate = 0.5:1 | 10 |
| Dichloromethane:ethyl acetate = 0.25:1 | 10 |
| Dichloromethane:methanol = 4:1 | 10 |
| Dichloromethane:methanol = 2:1 | 10 |
| Dichloromethane:methanol = 1:1 | 10 |
| Dichloromethane:methanol = 0:1 | 10 |

Example 20
Separation of the Extracts According to Example 18 Into Biologically Active Fractions Using Sephadex Methods: The ethyl acetate phase according to Example 18 was fractionated through Sephadex LH-20 using methanol as the solvent.

Result: Six fractions were obtained which are antibacterially active to varying extents (Table 14)

TABLE 14

Extracts obtainable from the ethyl acetate phase by separation on Sephadex

| Fraction | Activity against S. aureus (inhibition halo in mm) |
|---|---|
| A | 10 |
| B | 10 |
| C | 15 |
| D | 20 |
| E | 25 |
| F | 10 |

Example 21
Isolation of 3,26-Dihydroxylanosta-8,24-diene-7-one (Ganoderone B)

Methods: 400 mg of the dichloromethane extract of the fruit body was dissolved in the mobile phase and separated on Sephadex LH-20 (LKB Pharmacia, Uppsala, Sweden), with a mobile phase of n-hexane:dichloromethane 2:7 and a flow rate of 24 ml/h. After 24 h, rinsing with methanol was performed. According to thin-layer chromatographic monitoring, fractions having the same composition were combined. The fraction having an Rf value of 0.38 was further purified on Sephadex LH-20 (LKB Pharmacia, Uppsala, Sweden) with a mobile phase of methanol:water= 4:1. The substance recovered was recrystallized from methanol.

Result: An as yet unknown substance having a melting point of 165° C. was isolated. According to its spectra, it was identified as 3,26-dihydroxylanosta-8,24-diene-7-one and referred to as ganoderone B.

Example 22
Isolation of 2-[2-(2,5-dihydroxyphenyl)ethylidene]-11-hydroxy-6,10-dimethylun-deca-5,9-dienic Acid (Ganomycin A)

Methods: 400 mg of the dichloromethane extract of the fruit body was dissolved in the mobile phase and separated on Sephadex LH-20 (LKB Pharmacia, Uppsala, Sweden), with a mobile phase of n-hexane:dichloromethane 2:7 and a flow rate of 24 ml/h. After 24 h, rinsing with methanol was performed. According to thin-layer chromatographic monitoring, fractions having the same composition were combined. The fraction having an Rf value of 0.44 was rechromatographed on Sephadex LH-20 with dichloromethane and methanol=4:1 as the solvent. Further purification was performed with methanol as the solvent at a flow rate of 12 ml/h.

Result: An as yet unknown substance in the form of a yellow oil was isolated. According to its spectra, it was identified as 2-[2-(2,5-dihydroxyphenyl)ethylidene]-11-hydroxy-6,10-dimethylundeca-5,9-dienic acid and referred to as ganomycin A.

Example 23
Recovery of 2-[2-(2,5-dihydroxyphenyl)ethylidene]-6, 10-dimethylundeca-5,9-dienic Acid (Ganomycin B) as a Further Active Substance of Formula 1 From *G. pfeifferi*

Methods: 400 mg of the dichloromethane extract of the fruit body was dissolved in the mobile phase and separated on Sephadex LH-20 (LKB Pharmacia, Uppsala, Sweden), with a mobile phase of n-hexane:dichloromethane 2:7 and a flow rate of 24 ml/h. Further purification was performed with the solvent methanol:water 2:1. The fraction having an $R_f$ value of 0.58 was purified by column chromatography on Sephadex LH-20 with the solvent acetone:dichloromethane=2:1.

Result: An as yet unknown substance in the form of a yellow oil was isolated. According to its spectra, it was identified as 2-[2-(2,5-dihydroxyphenyl)ethylidene]-6,10-dimethylundeca-5,9-dienic acid and referred to as ganomycin B.

Example 24
Synthesis of Ganomycin B

At −78° C. under an inert gas atmosphere, 5.13 g (28.14 mmol) of 2-(phenylthio)-acetic acid methyl ester dissolved in 35 ml of THF was added to 42 ml of a 0.67 M solution of lithium diisopropylamide (prepared from n-butyllithium and diisopropylamine) in THF (corresponding to 28.14 mmol of LDA). After 40 minutes of stirring at this temperature, 3.55 g (11.00 mmol) of homogeranyl tosylate dissolved in 20 ml of DMSO is added. The solution is warmed up to room temperature and stirred for another 18 hours. For working up, 25 ml of saturated aqueous $NH_4Cl$ solution is added. This is followed by extracting three times with 30 ml each of dichloromethane, and the combined organic phases are successively washed with 20 ml each of saturated aqueous $CuSO_4$ solution, saturated aqueous NaCl solution and distilled water, and dried over $MgSO_4$. The residue remaining after the removal of the solvent is purified by column chromatography (mobile system heptane:ethyl acetate=7:1). The yield was 2.34 g (7.04 mmol, 64%) of (5E)-6,10-dimethyl-2-(phenylthio)-5,9-undecadieneic acid methyl ester. This compound is dissolved in 8.5 ml of THF and added to 10.5 ml of a 0.67 M solution of lithium diisopropylamide (prepared from n-butyllithium and diisopropylamine) in THF (corresponding to 7.04 mmol of LDA) at −78° C. under an inert gas atmosphere. After 40 minutes of stirring at this temperature, the solution is transferred with a syringe into a flask temperature-controlled at 0° C. in which 1.34 g (9.86 mmol) of freshly remolten zinc chloride had been charged. Now, the solution is stirred at 0° C. until almost all of the zinc chloride has dissolved (about 10 minutes), followed by the addition of 4.80 g (12.61 mmol) of [2,5-bis[(tert.-butyldimethylsilyl)oxy]-phenyl] acetaldehyde dissolved in 5 ml of THF. After another 10 minutes of stirring, 25 ml of saturated aqueous $NH_4Cl$ solution is added. This is followed by extracting three times with 30 ml each of dichloromethane, and the combined organic phases are successively washed with 20 ml each of saturated aqueous $CuSO_4$ solution, saturated aqueous NaCl solution and distilled water, and dried over $MgSO_4$. The residue remaining after the removal of the solvent is taken up in 15 ml of acetone. To this solution are successively added 1.28 g (6.00 mmol) of N-ethyl-2-fluoro-pyridinium tetrafluoroborate and 0.84 ml (6.00 mmol) of freshly distilled triethylamine. After 5–10 minutes of stirring at room temperature, 0.87 g (6.50 mmol) of lithium iodide is added. The reaction mixture is heated to 60° C. and stirred at this temperature for 1 hour. After cooling to room temperature, 50 ml of dichloromethane is added. The solution is washed twice with 15 ml each of saturated aqueous $CuSO_4$ solution and then with 15 ml of distilled water, and dried over $MgSO_4$. Purification of the residue remaining after distilling off the solvent by column chromatography (mobile system heptane:ethyl acetate=10:1) yields the two isomers (2(1')Z,5E)- and (2(1')E,5E)-2-[2'-(2,5-bis[(tert.-butyldimethylsilyl)-oxy]phenyl)ethylidene]-6,10-dimethyl-5,9-undecadienic acid methyl ester in a ratio of 45:55 in favor of the (2(1')E,5E) isomer and an overall yield of 48%.

To cleave the ester function, 0.20 g of (2(1')Z,5E,9E)-2-[2'-(2,5-bis[(tert.-butyl-dimethylsilyl)oxy]phenyl) ethylidene]-6,10-dimethyl-5,9-undecadienic acid methyl ester is heated in a solution of 1.00 g of potassium hydroxide in 10 ml of 96% ethanol for 4 hours under reflux. The reaction mixture, after cooling to room temperature, is poured onto 50 ml of ice water to which 3 ml of concentrated sulfuric acid has been added. The product is extracted three times with 15 ml each of ether. The combined organic phases are washed with 15 ml of saturated aqueous NaCl solution, dried over $MgSO_4$ and concentrated under reduced pressure. Purification of the product is effected by column chromatography (mobile system heptane:ethyl acetate=6:1). The yield was 87% of (2(1')Z,5E,9E)-2-[2'-(2,5-bis[(tert.-butyldimethylsilyl)oxy]phenyl)ethylidene]-6,10-dimethyl-5,9-undecadienic acid.

To cleave off the tert.-butyldimethylsilyl groups, 0,10 g of [2'-(2,5-bis[(tert.-butyldimethylsilyl)oxy]phenyl) ethylidene]-6,10-dimethyl-5,9-undecadienic acid is dissolved in 10 ml of DMF together with 2 equivalents of anhydrous potassium fluoride and 0.2 equivalents of 48% aqueous HBr, followed by stirring at room temperature for 24 hours under an argon atmosphere. Then, 10 ml of 2.0 M aqueous HCl solution is added, and the reaction mixture is extracted three times with 15 ml each of ether. The combined organic phases are washed with 10 ml of saturated aqueous NaCl solution, dried over $MgSO_4$ and concentrated under reduced pressure. Purification of the raw product is effected by column chromatography (mobile system heptane:ethyl acetate=1:1). The yield was 87% of ganomycin B.

Example 25
Preparation of Ganomycin B via Organometallic Intermediates

Methods: Under an argon atmosphere, 5.82 g (22.00 mmol) of tert.-butyldimethylsilyl triflate is slowly added with a syringe to a solution, temperature-controlled at 0° C., of 1.10 g (10.00 mmol) of 1,4-hydroquinone and 3.05 ml (22.00 mmol) of triethylamine in 20 ml of chloroform. After warming of the reaction solution to room temperature, it is stirred for 18 hours and then poured onto 50 ml of ice water. The organic phase is separated off, and the aqueous phase is extracted with 100 ml of chloroform. The combined organic phases are successively washed with 100 ml each of 1 M aqueous HCl, 1 M aqueous NaOH and saturated aqueous hydrogencarbonate solution, and dried over $MgSO_4$. After removal of the solvent under reduced pressure, the product is purified by distillation. The yield was 3.05 g (9.00 mmol, 90%) of 1,4-bis[(tert.-butyldimethylsilyl)-oxy]benzene.

In a second reaction step, this intermediate is dissolved in 40 ml of carbon tetrachloride and cooled down to 0° C. With vigorous stirring, 3.70 ml (7.20 mmol) of bromine in 10 ml of carbon tetrachloride is slowly added dropwise in such a way that the temperature of the reaction solution does not exceed 5° C. After completion of the addition, stirring is continued at this temperature for 2 hours, and then, for working up, the solution is successively washed with 15 ml each of distilled water, 3% aqueous thiosulfate solution, 10% aqueous NaOH solution and again with distilled water. The raw product obtained after removal of the solvent under reduced pressure is recrystallized from chloroform/acetonitrile. The yield was 2.25 g (5.40 mmol, 60%) of 1,4-bis[(tert.-butyldimethylsilyl)oxy]-2-bromobenzene.

The next reaction step involves the preparation of a Grignard compound. Thus, 0.13 g (5.40 mmol) of magnesium turnings and 0.25 g (0.60 mmol) of 1,4-bis[(tert.-butyldimethylsilyl)oxy]-2-bromobenzene in 10 ml of absolute ether are charged into a three-necked flask equipped with a reflux condenser. The onset of the reaction can be seen from a clouding and heating of the solution. Then, with vigorous stirring, 2.00 g (4.80 mmol) of 1,4-bis[(tert.-butyldimethylsilyl)oxy]-2-bromobenzene dissolved in 100 ml of absolute ether is slowly added dropwise to keep the ether slightly boiling. After completion of the addition, the mixture is heated under reflux for about 30 minutes until almost all of the magnesium has dissolved. The ethereal solution of the in-situ produced [2,5-bis[(tert.-butyldimethylsilyl)oxy]phenyl]magnesium bromide (5.40 mmol) is diluted with 30 ml of THF, cooled down to −30° C., and 2.50 ml of a 0,10 M solution of dilithium tetrachlorocuprate is added dropwise. After 30 minutes of stirring at this temperature, the whole solution is added dropwise to a solution in 30 ml of THF, cooled down to −30° C., of 1.44 g (5.40 mmol) of (E)-6,10-dimethyl-2-oxiranylundeca-5,9-diene-carboxylic acid methyl ester, whose synthesis is described in the following. After about 2 hours of stirring at the stated temperature, the reaction is completed, and for working up, 10 ml of saturated aqueous $NH_4Cl$ solution and 15 ml of distilled water are added. After the phases have separated, the aqueous phase is again extracted with 20 ml of ether, the combined organic phases are washed twice with 15 ml each of saturated aqueous NaCl solution, and dried over $MgSO_4$. The residue obtained after distilling off the solvent is purified by column chromatography (mobile system heptane:ethyl acetate=9:1). The yield was 1.83 g (3.02 mmol, 56%) of (5E)-2-[2'-(2,5-bis[(tert.-butyldimethylsilyl) oxy]phenyl)-1'-hydroxyethyl]-6,10-dimethyl-5,9-undecadienic acid methyl ester.

To a solution, cooled down to 0° C., of 1.64 g (2.72 mmol) of (5E)-2-[2'-(2,5-bis[(tert.-butyldimethylsilyl)oxy]phenyl)-1'-hydroxyethyl]-6,10-dimethyl-5,9-undecadienic acid methyl ester and 1.52 ml (10.90 mmol) of triethylamine in 8 ml of dichloromethane is added 0.42 ml (5.50 mmol) of methanesulfonic acid chloride. The reaction mixture is stirred at room temperature for 3 hours, then diluted with 20 ml of dichloromethane and successively washed with 10 ml each of saturated aqueous $NaHCO_3$ solution, 0.10 M aqueous HCl solution and saturated aqueous NaCl solution. After drying of the organic phase over $MgSO_4$, the solvent is distilled off under reduced pressure, the remaining residue is taken up in 8 ml of toluene, and 1.2 ml (8.20 mmol) of 1,8-diazabicyclo[5.4.0]undecene (DBU) is added. The solution is stirred for 12 hours at a temperature of 80° C., then diluted with 15 ml of ether and successively washed with 10 ml each of 0.10 M aqueous HCl solution, saturated aqueous $NaHCO_3$ solution and saturated aqueous NaCl solution. The residue obtained after drying the organic phase over $MgSO_4$ and removing the solvent is purified by column chromatography (mobile system heptane:ethyl acetate=10:1). The two isomers (2(1')Z,5E)- and (2(1')E,5E)-2-[2'-(2,5-bis-[(tert.-butyldimethylsilyl)oxy]phenyl)ethylidene]-6,10-dimethyl-5,9-undecadienic acid methyl ester are obtained in a ratio of 20:80 in favor of the (2(1')E,5E)-isomer and in an overall yield of 83%.

For the synthesis of the (E)-6,10-dimethyl-2-oxiranylundeca-5,9-dienecarboxylic acid methyl ester, 27.00 ml (54.00 mmol) of a 2 M solution of allylmagnesium chloride in ether is added dropwise within 30 minutes to a solution of 1.10 g (6.40 mmol) of geranyl chloride in 50 ml of THF/HMPT (v/v=1/1). The resulting mixture is stirred at room temperature for 15 hours, and then 20 ml of saturated aqueous $NH_4Cl$ solution is added. The organic phase is separated off, and the aqueous phase is extracted four times with 25 ml each of dichloromethane. The combined organic phases are concentrated under reduced pressure. The remaining residue is taken up with 50 ml of ether, successively washed with 2 M aqueous hydrochloric acid, saturated aqueous NaCl solution and distilled water, dried over $MgSO_4$ and concentrated under reduced pressure. The vacuum distillation of the thus obtained residue yields 0.89 g (4.99 mmol, 78%) of (E)-6,10-dimethyl-undeca-1,5,9-triene.

Within 10 minutes, 24.70 ml (12.40 mmol) of a 0.5 M solution of bis(3-methyl-butane-2-yl)borane in ether at 0–5° C. is added dropwise to a well stirred solution of 2.00 g (11.20 mmol) of (E)-6,10-dimethylundeca-1,5,9-triene in 25 ml of THF.

The reaction mixture is stirred for 15 hours, and then 3.50 ml of 3 M aqueous NaOH solution and 3.50 ml of 30% aqueous hydrogen peroxide solution are added. After one hour of stirring, the mixture is neutralized with 10.00 ml of aqueous saturated $NH_4Cl$ solution, and the aqueous phase extracted three times with 20.00 ml each of ether. The combined organic phases are dried over $MgSO_4$ and concentrated under reduced pressure. The thus obtained raw product is purified by column chromatography (mobile system heptane:ether=7:3). The yield was 0.85 g (4.26 mmol, 38%) of (E)-6,10-dimethylundeca-5,9-diene-1-ol as a colorless oil.

At room temperature, 3.50 g (8.90 mmol) of pyridinium dichromate was added to a solution of 0.50 g (2.60 mmol) of (E)-6,10-dimethylundeca-5,9-diene-1-ol in 15 ml of DMF. After 20 hours of stirring, the whole solution is poured onto 80 ml of ice water and extracted three times with 60 ml each of ether. The combined organic extracts are dried over $MgSO_4$ and purified by column chromatography (mobile system heptane:ether=7:3). The yield was 0.17 g (0.81 mmol, 31%) of (E)-6,10-dimethylundeca-5,9-dienecarboxylic acid as a colorless oil.

1.70 g (8.08 mmol) of (E)-6,10-dimethylundeca-5,9-dienecarboxylic acid is dissolved in 10 ml of methanol/water (v/v=10/1), and with stirring, 1.0 M ethereal diazomethane solution is added dropwise until nitrogen evolution can no longer be observed. The residue remaining after removal of the solvent mixture is purified by column chromatography (mobile system heptane:ether=7:1). The yield was 1.68 g (7.49 mmol, 93%) of (E)-6,10-dimethylundeca-5,9-dienecarboxylic acid methyl ester as a colorless oil.

To 14 ml of a 0.67 M solution of lithium diisopropylamide (prepared from n-butyl-lithium and diisopropylamine) in THF (corresponding to 8.92 mmol of LDA) is added dropwise 1.50 g (6.69 mmol) of (E)-6,10-dimethylundeca-5,9-dienecarboxylic acid methyl ester dissolved in 3 ml of THF at −78° C. under an inert gas atmosphere. Within one hour, the solution is warmed up to −50° C., and then 0.83 g (11.15 mmol) of formic acid ethyl ester is added, and stirring is performed for another hour at the stated temperature. For working up, the whole reaction solution is poured onto 50 ml of ice water and extracted three times with 15 ml each of ether. The combined organic phases were washed with 20 ml of distilled water and dried over $MgSO_4$. The residue remaining after the removal of the solvent can be purified by column chromatography (mobile system heptane:ether=7:1) or by vacuum distillation. The yield was 1.12 g (4.42 mmol, 66%) of (E)-6,10-dimethyl-2-formylundeca-5,9-dienecarboxylic acid methyl ester as a colorless oil.

Under an inert gas atmosphere, 0.20 g (4.10 mmol) of a 50% sodium hydride/oil dispersion in a frit is washed twice with 10 ml each of dry hexane. The NaH freed from oil is transferred to a three-necked flask under inert gas, 20 ml of dry DMSO is added, and the mixture is heated at 60° C. for one hour with stirring. After the addition of 25 ml of THF, the reaction mixture is cooled down to 0° C., and by means of a syringe, there are added first 0.90 g (4.10 mmol) of trimethylsulfonium iodide dissolved in 20 ml of dry DMSO and then 1.06 g (4.20 mmol) of (E)-6,10-dimethyl-2-formylundeca-5,9-dienecarboxylic acid methyl ester dissolved in 15 ml of THF. After 48 hours of stirring at room temperature, the reaction is complete. The reaction mixture is poured onto 300 ml of ice water and extracted three times with 30 ml each of ether. The combined organic phases are washed twice with 20 ml each of distilled water and dried over $MgSO_4$. The residue obtained after distilling off the solvent under reduced pressure is purified over a short frit column (mobile system heptane:ether=7:1). The yield was 0.80 g (2.99 mmol, 73%) of (E)-6,10-dimethyl-2-oxiranylundeca-5,9-dienecarboxylic acid methyl ester as a colorless oil.

Result: Deprotection is effected as described in Example 24 to yield ganomycin B.

Example 26
Synthesis of Ganomycin B by Starting From 1,4-bis[(tert.-butyldimethylsilyl)oxy]-2-methylbenzene Methods: To a solution, temperature-controlled at 0° C., of 1.24 g (10.00 mmol) of 1,4-dihydroxy-2-methylbenzene and 3.05 ml (22.00 mmol) of triethylamine in 20 ml of chloroform is slowly added with a syringe 5.82 g (22.00 mmol) of tert.-butyldimethylsilyl triflate under an argon atmosphere. After having heated up to room temperature, the reaction solution is stirred for 18 hours and subsequently poured onto 50 ml of ice water. The organic phase is separated off, and the aqueous phase is extracted with 100 ml of chloroform. The combined organic phases are successively washed with 100 ml each of 1 M aqueous HCl, 1 M aqueous NaOH and saturated aqueous hydrogencarbonate solution, and dried over $MgSO_4$. After removal of the solvent under reduced pressure, the product is purified by recrystallization from chloroform/acetonitrile. The yield was 3.35 g (9.50 mmol, 95%) of 1,4-bis[(tert.-butyldimethylsilyl)oxy]-2-methylbenzene.

This intermediate is heated with 1.77 g (9.97 mmol) of N-bromosuccinimide and 20 mg of benzoyl peroxide in 20 ml of carbon tetrachloride for 2 hours under reflux. The solid precipitating after the solution has cooled is filtered off and washed twice with 10 ml each of carbon tetrachloride. The filtrates are combined, and the solid remaining after removal of the solvent under reduced pressure is recrystallized from petroleum ether. The yield was 3.03 g (7.03 mmol, 74%) of 1,4-bis[(tert.-butyldimethylsilyl)oxy]-2-bromomethylbenzene. This is in turn used for preparing a Grignard compound. In a three-necked flask equipped with a reflux condenser, 0.13 g (5.40 mmol) of magnesium turnings and 0.26 g (0.60 mmol) of 1,4-bis[(tert.-butyldimethylsilyl)oxy]-2-bromomethylbenzene are charged in 10 ml of absolute ether. The onset of the reaction can be seen from a clouding and heating of the solution. Then, with vigorous stirring, 2.00 g (4.80 mmol) of 1,4-bis[(tert.-butyldimethylsilyl)oxy]-2-bromobenzene dissolved in 100 ml of absolute ether is slowly added dropwise to keep the ether slightly boiling. After completion of the addition, the mixture is heated under reflux for about 30 minutes until almost all of the magnesium has dissolved.

The ethereal solution of the in-situ produced [2,5-bis[(tert.-butyldimethylsilyl)-oxy]phenyl]methylmagnesium bromide (5.40 mmol) is diluted with 30 ml of THF, cooled down to −30° C., and 2.50 ml of a 0,10 M solution of dilithium tetrachlorocuprate is added dropwise. After 30 minutes of stirring at this temperature, the whole solution is added dropwise to a solution in 30 ml of THF, cooled down to −30° C., of 1.37 g (5.40 mmol) of (E)-6,10-dimethyl-2-formylundeca-5,9-dienecarboxylic acid methyl ester, whose synthesis has been described in Example 25.

After about 2 hours of stirring at the stated temperature, the reaction is completed, and for working up, 10 ml of saturated aqueous $NH_4Cl$ solution and 15 ml of distilled water are added. After the phases have separated, the aqueous phase is again extracted with 20 ml of ether, the combined organic phases are washed twice with 15 ml each of saturated aqueous NaCl solution, and dried over $MgSO_4$. The residue obtained after distilling off the solvent is purified by column chromatography (mobile system heptane:ethyl acetate=9:1). The yield was 1.83 g (3.02 mmol, 56%) of (5E)-2-[2'-(2,5-bis[(tert.-butyldimethylsilyl)oxy]phenyl)-1'-hydroxyethyl]-6,10-dimethyl-5,9-undecadienic acid methyl ester.

The dehydration is effected as described in Example 25 to yield the two isomers (2(1')Z,5E)- and (2(1')E,5E)-2-[2'-(2,5-bis[(tert.-butyldimethylsilyl)oxy]phenyl)-ethylidene]-6,10-dimethyl-5,9-undecadienic acid methyl ester in a ratio of 20:80 in favor of the (2(1')E,5E)-isomer and in an overall yield of 83%.

Result: Deprotection is effected as described in Example 24 to yield ganomycin B.

Example 27
Synthesis of Ganomycin B by Starting From Terpenoid Phenylsulfones

Methods: A mixture of 4.76 g (12.50 mmol) of [2,5-bis[(tert.-butyldimethylsilyl)-oxy]phenyl]acetaldehyde, 2.15 ml (25.00 mmol) of acrylic acid methyl ester and 0.28 g (2.50 mmol) of 1,4-diazabicyclo[2.2.2]octane is stirred at room temperature for 40 days. The residue remaining after the removal of the excess acrylic acid methyl ester is purified by column chromatography (mobile system heptane:ethyl acetate=10:1). The yield was 3.21 g (6.88 mmol, 55%) of 4-[2,5-bis[(tert.-butyldimethylsilyl)oxy]phenyl]-3-hydroxy-2-methylidenebutanoic acid methyl ester.

At room temperature, 2.80 ml (34.86 mmol) of pyridine, 2.00 ml (21.34 mmol) of acetic anhydride and 30 mg (0.24 mmol) of 4-(dimethylamino)pyridine are added to a solution of 3.21 g (6.88 mmol) of 4-[2,5-bis[(tert.-butyldimethylsilyl)oxy]phenyl]-3-hydroxy-2-methylidenebutanoic acid methyl ester in 80 ml of dichloromethane. The solution is stirred for two hours and then poured onto 20 ml of saturated aqueous $NH_4Cl$ solution, the organic phase is washed first twice with 10 ml each of saturated aqueous $CuSO_4$ solution and then twice with 10 ml each of saturated aqueous NaCl solution, and dried over $MgSO_4$. After distilling off the solvent, the raw product is purified by column chromatography (mobile system heptane:ethyl acetate=10:1). The yield was 3.26 g (6.40 mmol, 93%) of 4-[2,5-bis[(tert.-butyidimethylsilyl)oxy]phenyl]-3-acetoxy-2-methylidenebutanoic acid methyl ester.

This intermediate is reacted with a sulfone which is obtained as follows. To a slurry of 3.78 g (23.03 mmol) of sodium benzenesulfinate in 20 ml of DMF is added with stirring a solution of 5.00 g (23.03 mmol) of geranyl bromide in 5 ml of DMF. The mixture is heated at 120° C. for 2 hours, cooled down, and 100 g of ice water is added. The solution is subsequently extracted three times with 20 ml each of dichloromethane, the combined organic phases are washed first twice with 15 ml each of saturated aqueous $CuSO_4$ solution and then with 15 ml of distilled water, and dried over $MgSO_4$. The residue remaining after the removal of the solvent under reduced pressure is purified by column chromatography (mobile system heptane:ethyl acetate=10:1). The yield was 4.74 g (17.04 mmol, 74%) of [(2E, 6E)-3,7-dimethyl-2,6-octadienyl]phenylsulfone.

To a solution of 2.20 g (7.90 mmol) of [(2E,6E)-3,7-dimethyl-2,6-octadienyl]-phenylsulfone in THF/1,3-dimethyl-3,4,5,6-tetrahydro-2(1H)pyrimidinone (49 ml/12 ml) is added dropwise at −78° C. under an argon atmosphere 15.2 ml of a 1.30 M solution of n-butyllithium in hexane (19.8 mmol). The reaction mixture is stirred for 20 minutes at the stated temperature, followed by the dropwise addition within one hour of 4.02 g (7.90 mmol) of 4-[2,5-bis[(tert.-butyldimethylsilyl)oxy]-phenyl]-3-acetoxy-2-methylidenebutanoic acid methyl ester dissolved in 20 ml of THF. With stirring, the solution is warmed up to −30° C. within 2 hours, 60 ml of saturated aqueous $NH_4Cl$ solution is added, and the mixture is extracted four times with 20 ml each of ether. The combined organic phases are washed with 15 ml of saturated aqueous NaCl solution and dried over $MgSO_4$. Purification of the residue remaining after distilling off the solvent by column chromatography (mobile system heptane:ethyl acetate=10:1) yields the two isomers (2(1')Z, 5E)- and (2(1')E,5E)-2-[2'-(2,5-bis[(tert.-butyldimethylsilyl) oxy]phenyl)ethylidene]-6,10-dimethyl-4-phenylsulfonyl-5,9-undecadienic acid methyl ester in a ratio of 27:73 in favor of the (2(1')E,5E) isomer and an overall yield of 68%.

To a solution of 0.25 g (0.34 mmol) of (2(1')Z,5E)-2-[2'-(2,5-bis[(tert.-butyl-dimethylsilyl)oxy]phenyl)ethylidene]-6,10-dimethyl-4-phenylsulfonyl-5,9-undecadienic acid methyl ester in 9 ml of THF is added a solution of $PdCl_2$/(dppp) (61 mg, 0.10 mmol) in 2.5 ml of THF. The reaction mixture is temperature-controlled at 0° C., and within 3.5 hours, 3.4 ml of a 1.0 M solution of lithium triethylborohydride in THF is added. After another 2.5 hours of stirring at the stated temperature, the reaction mixture is diluted with 35 ml of ether and washed with 10 ml each of 1.0 M aqueous NaCN solution and with saturated aqueous NaCl solution. The organic phase is dried over magnesium sulfate and concentrated under reduced pressure. The purification of the remaining residue is effected by column chromatography (mobile system heptane:ethyl acetate=10:1). The yield was 0.10 g (0.17 mmol, 50%) of (2(1')Z,5E)-2-[2'-(2,5-bis[(tert.-butyldimethylsilyl)oxy]phenyl)ethylidene]-6,10-dimethyl-5,9-undecadienic acid methyl ester.

Result: Deprotection is effected as described in Example 24 to yield ganomycin B.

Example 28

Synthesis of Ganomycin A

For the synthesis of [(4E,8E)-5,9-dimethyl-10-[(tert.-butyidimethylsilyl)oxy]-4,8-decadienyl] triphenylphosphonium iodide required as an intermediate, 2.83 g (25.47 mmol) of selenium dioxide is added to a solution of 5.00 g (25.47 mmol) of geranyl acetate in 20 ml of 95% ethanol. The solution is heated under reflux for one hour. The cooled solution is filtered and concentrated under reduced pressure. The remaining residue is taken up in 20 ml of dry dichloromethane, 1.16 g (30.56 mmol) of sodium borohydride is added, and the mixture is stirred for 10 minutes at room temperature. For working up, 20 ml of distilled water is carefully added, and then the organic phase is washed first with 10 ml of 3% aqueous $NaHSO_4$ solution and then with 10 ml of distilled water. After drying over $MgSO_4$ and removing the solvent under reduced pressure, 8-hydroxygeranyl acetate is obtained (3.30 g, 15.54 mmol, 61%) which is taken up in 10 ml of dry DMF, then 2.81 g (18.65 mmol) of tert.-butyldimethylsilyl chloride and 2.64 g (38.85 mmol) are added, and the mixture is stirred for 15 hours at 35° C. The whole solution is poured onto 15 ml of ice water and extracted twice with 10 ml each of dichloromethane. The combined organic phases are washed first with 10 ml of 3% aqueous $NaHSO_4$ solution and then with 10 ml of distilled water, dried over $MgSO_4$ and concentrated under reduced pressure. The thus obtained residue is taken up in 10 ml of 1% methanolic sodium methanolate solution and stirred for 10 hours at room temperature. After neutralization of the solution with acidic ion exchangers and removal of the solvent under reduced pressure, 8-[(tert.-butyidimethylsilyl)-oxy]geraniol is obtained in an overall yield of 3.99 g (14.01 mmol), which is then added to 2 ml of freshly distilled 2,6-lutidine. The solution obtained is slowly added dropwise at 0° C. to a vigorously stirred suspension of 0.62 g (14.70 mmol) of dry LiCl in 7.5 ml of DMF. After about 30 minutes, a white bulky precipitate forms to which 1.13 ml (14.70 mmol) of methanesulfonyl chloride is added. After 6 hours of stirring at room temperature, the whole solution is poured onto 50 ml of ice water and extracted twice with 75 ml each of ether. The combined organic phases are washed first with 30 ml of distilled water, then with 30 ml of saturated aqueous $CuSO_4$ solution, and finally with 30 ml of saturated aqueous NaCl solution, and dried over $MgSO_4$. After removal of the solvent, the [(2E,6E)-2,6-dimethyl-8-chloro-2,6-octadienyl] (tert.-butyldimethylsilyl) ether is obtained as a slightly yellow oil in an overall yield of 52% (4.01 g, 13.24 mmol).

To a suspension, cooled down to −78° C., of 1.52 g (8.00 mmol) of copper(I) iodide in 40 ml of THF is added slowly with stirring 43.2 ml of a 0.7 M solution of vinylmagnesium bromide in THF. The suspension is stirred for 20 minutes, then warmed up to −25° C. and stirred at this temperature for another 35 minutes. To the thus obtained olive solution is added dropwise 4.01 g (13.24 mmol) of the [(2E,6E)-2,6-dimethyl-8-chloro-2,6-octadienyl](tert.-butyldimethylsilyl) ether dissolved in 2 ml of THF. After 6 hours of stirring at room temperature, 150 ml of ether is added, and the organic phase is successively washed with 50 ml each of distilled water, 3% aqueous $NH_4Cl$ solution, saturated aqueous $CuSO_4$ solution and saturated aqueous NaCl solution, and dried over MgSO$_4$. The residue obtained after distilling off the solvent under reduced pressure is purified by column chromatography (mobile system heptane). The yield was 3.04 g (10.19 mmol, 77%) of [(2E,6E)-2,6-dimethyl-2,6,9-decatrienyl](tert.-butyidimethylsilyl) ether.

To 18 ml of a freshly prepared 1.2 M solution of disiamylborane in THF, cooled down to −10° C., is added dropwise 3.04 g (10.19 mmol) of [(2E,6E)-2,6-dimethyl-2,6,9-decatrienyl](tert.-butyidimethylsilyl) ether dissolved in 3 ml of THF. The yellow solution obtained is vigorously stirred for 5.5 hours. Subsequently, 7 ml of distilled water, 7 ml of 3 M aqueous NaOH solution and 7 ml of 30% aqueous hydrogen peroxide are successively added dropwise. After 18 hours of stirring at room temperature, 190 ml of ether is added, the organic phase is washed three times with 30 ml each of distilled water, and dried over MgSO$_4$. The residue obtained after removal of the solvent under reduced pressure is purified by column chromatography (mobile system heptane:ether=20:1). The yield was 2.63 g (8.46 mmol, 83%) of (4E,8E)-5,9-dimethyl-10-[(tert.-butyldimethylsilyl)oxy]-4,8-decadiene-1-ol.

To a solution, cooled down to 0° C., of 2.63 g (8.46 mmol) of (4E,8E)-5,9-dimethyl-10-[(tert.-butyidimethylsilyl)oxy]-4,8-decadiene-1-ol, 2.89 g (11.00 mmol) of triphenylphosphine and 0.80 g (11.55 mmol) of imidazole in 15 ml of ether and 10 ml of acetonitrile is slowly added 3.08 g (12.10 mmol) of iodine. After 45 minutes of stirring, 150 ml of ether is added. The organic phase is successively washed with 30 ml each of saturated aqueous sodium thiosulfate solution, saturated aqueous CuSO$_4$ solution and distilled water, and dried over MgSO$_4$. The residue obtained after distilling off the solvent is taken up in 10 ml of benzene, 2.47 g (9.36 mmol) of triphenylphosphine is added, and the mixture is heated under reflux for 24 hours. The solid remaining after cooling down is taken up in 100 ml of dichloromethane, and the solvent is subsequently distilled off under reduced pressure. The remaining oil is induced to crystallize by the addition of dry ether. The yield was 4.64 g (6.77 mmol, 80%) of the phosphonium salt.

To a solution, cooled down to −78° C., of 2.06 g (3.00 mmol) of [(4E,8E)-5,9-dimethyl-10-[(tert.-butyldimethylsilyl)oxy]-4,8-decadienyl]triphenylphosphonium iodide in 10 ml of THF is slowly added 9.2 ml of a 0.65 M solution of potassium bis(trimethylsilyl)amide (6.00 mmol) in toluene. After 1.5 hours of stirring at the stated temperature, 240 µl (3.20 mmol) of chloroformic acid methyl ester is added. The solution is stirred at −78° C. for another 30 minutes, then slowly warmed up to room temperature and again stirred for 1.5 hours. After the addition of 0.92 g (2.42 mmol) of [2,5-bis[(tert.-butyldimethylsilyl)oxy]phenyl]acetaldehyde dissolved in 3 ml of THF, the solution is stirred at room temperature for 32 hours, then diluted with 25 ml of ether and successively washed with 10 ml each of saturated aqueous NH$_4$Cl solution and distilled water. The residue remaining after drying the organic phase over MgSO$_4$ and distilling off the solvent is purified by column chromatography (mobile system heptane:ethyl acetate=10:1). The two isomers, (2(1')Z,5E,9E)- and (2(1')E,5E,9E)-2-[2'-(2,5-bis[(tert.-butyldimethylsilyl)oxy]phenyl)ethylidene]-6,10-dimethyl-11-[(tert.-butyldimethylsilyl)oxy]-5,9-undecadienic acid methyl ester, are obtained in a ratio of 14:86 in favor of the (2(1')E,5E,9E) isomer and in an overall yield of 54%.

The deprotection of the terminal OH function of the terpenoid side chain is effected by adding 2 equivalents of 50% aqueous HF solution to a solution, cooled down to 0° C., of 0.50 g of (2(1')Z,5E,9E)-2-[2'-(2,5-bis[(tert.-butyidimethylsilyl)oxy]phenyl)ethylidene]-6,10-dimethyl-11-[(tert.-butyldimethylsilyl)oxy]-5,9-undecadienic acid methyl ester in 15 ml of acetonitrile. After 1 hour, 10 ml of saturated aqueous NaHCO$_3$ solution is added, the reaction mixture is subsequently extracted three times with 10 ml each of ether, the combined organic phases are washed with saturated aqueous NaCl solution and dried over MgSO$_4$. The purification of the residue remaining after distilling off the solvent is effected by column chromatography (mobile system heptane:ethyl acetate=6:1). The yield was 92% of (5E,9E)-2-[2'-(2,5-bis[(tert.-butyldimethylsilyl)oxy]phenyl)ethylidene]-6,10-dimethyl-11-hydroxy-5,9-undecadienic acid methyl ester.

Result: The further deprotection is performed as described in Example 24 to yield ganomycin A.

Example 29

Synthesis of Ganomycin B by the Coupling of [2,5-bis[(tert.-butyldimethylsilyl)-oxy]phenyl]acetaldehyde With (E)-6,10-dimethylundeca-5,9-dienecarboxylic Acid Methyl Ester To a solution of 0.46 ml (3.30 mmol) of diisopropylamine in 3 ml of THF at 0° C. is added dropwise 1.39 ml of a 2.33 M ethereal solution of n-butyllithium (3.23 mmol). After 20 minutes of stirring at 0° C., the solution is cooled down to −78° C. By means of a syringe, there is added 0.66 g (2.95 mmol) of (E)-6,10-dimethylundeca-5,9-dienecarboxylic acid methyl ester, the synthesis of which has already been described in Example 25, dissolved in 3 ml of THF. After 1 hour of stirring at the stated temperature, 0.92 g (2.42 mmol) of [2,5-bis[(tert.-butyl-dimethylsilyl)oxy]phenyl]acetaldehyde dissolved in 3 ml of THF is added. After another hour of stirring at −78° C., the reaction is complete. For working up, 5 ml of saturated aqueous NH$_4$Cl solution is added, followed by warming up to room temperature. The reaction mixture is extracted three times with 5 ml each of ether, and the combined organic phases are washed twice with 5 ml each of saturated aqueous NaCl solution and dried over MgSO$_4$. The residue remaining after distilling off the solvent is purified by column chromatography (mobile system heptane:ethyl acetate=10:1). The yield was 1.14 g (1.89 mmol, 78%) of (5E)-2-[2'-(2,5-bis[(tert.-butyldimethylsilyl)oxy]phenyl)-1'-hydroxyethyl]-6,10-dimethyl-5,9-undecadienic acid methyl ester.

The dehydration is effected as described in Example 24 to yield the two isomers (2(1')Z,5E)- and (2(1')E,5E)-2-[2'-(2,5-bis[(tert.-butyidimethylsilyl)oxy]phenyl)-ethylidene]-6,10-dimethyl-5,9-undecadienic acid methyl ester in a ratio of 20:80 in favor of the (2(1')E,5E)-isomer and in a yield of 83%.

Result: Deprotection is effected as described in Example 24 to yield ganomycin B.

Example 30

Synthesis of Further Derivatives of Formula 1 by Varying the Sulfone Component

Methods: The 4-[2,5-bis[(tert.-butyldimethylsilyl)oxy]phenyl]-3-acetoxy-2-methylidenebutanoic acid methyl ester prepared according to Example 29 can be reacted with other sulfones, e.g., [(2E,6E)-3,7-dimethyl-8-[(tert.-butyldimethylsilyl)oxy]-2,6-octadienyl]phenylsulfone.

[(2E,6E)-3,7-Dimethyl-8-[(tert.-butyldimethylsilyl)oxy]-2,6-octadienyl]phenylsulfone can be obtained as follows: To a slurry of 2.17 g (13.24 mmol) of sodium benzenesulfinate in 15 ml of DMF is added with stirring a solution of 4.01 g (13.24 mmol) of [(2E,6E)-2,6-dimethyl-8-chloro-2,6-octadienyl](tert.-butyldimethylsilyl) ether, the synthesis of which has already been described in Example 28, in 4 ml of DMF. The mixture is heated at 120° C. for 2 hours, cooled down, and 70 g of ice water is added. The solution is subsequently extracted three times with 15 ml each of dichloromethane, and the combined organic phases are washed first twice with 10 ml each of saturated aqueous $CuSO_4$ solution, then with 10 ml of distilled water, and dried over $MgSO_4$. The residue remaining after removal of the solvent under reduced pressure is purified by column chromatography (mobile system heptane:ethyl acetate=10:1). The yield was 3.73 g (9.14 mmol, 69%) of [(2E,6E)-3,7-dimethyl-8-[(tert.-butyldimethylsilyl)oxy]-2,6-octadienyl]phenylsulfone.

Result: The reaction with [(2E,6E)-3,7-dimethyl-8-[(tert.-butyldimethylsilyl)oxy]-2,6-octadienyl]phenylsulfone, followed by deprotection as described in Examples 24 and 28, yields ganomycin A.

Example 31
Build-up of Long-chained Ganomycin Homologues

To a solution of 1.00 g (1.66 mmol) of (2(1')Z,5E,9E)-2-[2'-(2,5-bis[(tert.-butyl-dimethylsilyl)oxy]phenyl)ethylidene]-6,10-dimethyl-11-hydroxy-5,9-undecadienic acid methyl ester (preparation see Example 28), 0.20 g (4.77 mmol) of lithium chloride and 1.12 g (8.20 mmol) of collidine in 12 ml of DMF was added dropwise 0.4 ml (5.00 mmol) of mesyl chloride at −3° C. The mixture is warmed up to 3° C. within one hour and then poured onto 10 ml of saturated aqueous $NaHCO_3$ solution. The thus obtained solution is extracted three times with 10 ml each of heptane/ethyl acetate (v/v=1/1). The combined organic phases are dried over $MgSO_4$ and concentrated under reduced pressure. The thus obtained (2(1')Z,5E,9E)-2-[2'-(2,5-bis[(tert.-butyidimethylsilyl)oxy]phenyl)ethylidene]-6,10-dimethyl-11-chloro-5,9-undecadienic acid methyl ester is used for reaction without further purification.

To a solution of 0.61 g (1.50 mmol) [(2E,6E)-3,7-dimethyl-8-[(tert.-butyldimethylsilyl)oxy]-2,6-octadienyl]phenylsulfone (preparation see Example 30) in THF/1,3-dimethyl-3,4,5,6-tetrahydro-2(1H)-pyrimidinone (10 ml/3 ml) is added dropwise 2.9 ml of a 1.30 M solution of n-butyllithium in hexane (3.76 mmol) at −78° C. under an argon atmosphere. The reaction mixture is stirred at the stated temperature for 20 minutes, followed by the dropwise addition, within one hour, of (2(1')Z,5E,9E)-2-[2'-(2,5-bis[(tert.-butyldimethylsilyl)oxy]phenyl)ethylidene]-6,10-dimethyl-11-chloro-5,9-undecadienic acid methyl ester dissolved in 4 ml of THF. With stirring, the solution is warmed up to −30° C. within 2 hours, mixed with 10 ml of saturated aqueous $NH_4Cl$ solution and extracted four times with 5 ml each of ether. The combined organic phases are washed with 5 ml of saturated aqueous NaCl solution and dried over $MgSO_4$. Purification by column chromatography (mobile system heptane:ethyl acetate=10:1) of the residue remaining after distilling off the solvent gives (2(1')Z,5E,9E,13E,17E)-2-[2'-(2,5-bis[(tert.-butyl-dimethylsilyl)oxy]phenyl)ethylidene]-6,10,14,18-tetramethyl-11-phenylsulfonyl-19-[(tert.-butyldimethylsilyl)oxy]-5,9,13,17-nonadecatetraenic acid methyl ester in a yield of 66% (1.09 g, 1.09 mmol).

Result: The reduction of the phenylsulfonyl function is effected as described in Example 30 to yield the (2(1')Z,5E,9E,13E,17E)-2-[2'-(2,5-bis[(tert.-butyldimethylsilyl)oxy]phenyl)ethylidene]-6,10,14,18-tetramethyl-19-[(tert.-butyldimethylsilyl)oxy]-5,9,13,17-nonadecatetraenic acid methyl ester in 48% yield.

Now, starting with (2(1')Z,5E,9E,13E,17E)-2-[2'-(2,5-bis[(tert.-butyldimethylsilyl)-oxy]phenyl)ethylidene]-6,10,14,18-tetramethyl-19-[(tert.-butyldimethylsilyl)oxy]-5,9,13,17-nonadecatetraenic acid methyl ester, complete deprotection can be performed as described in Example 24.

Result: (2(1')Z,5E,9E,13E,17E)-2-[2'-(2,5-dihydroxyphenyl)ethylidene]-6,10,14,18-tetramethyl-19-hydroxy-5,9,13,17-nonadecatetraenic acid is obtained.

Another possibility is the cleavage only of the terminal tert.-butyidimethylsilyl group in accordance with Example 28.

Result: (2(1')Z,5E,9E,13E,17E)-2-[2'-(2,5-bis[(tert.-butyidimethylsilyl)oxy]phenyl)ethylidene]-6,10,14,18-tetramethyl-19-hydroxy-5,9,13,17-nonadecatetraenic acid methyl ester is obtained.

The latter can be again subjected to the reaction sequence described in this Example: chlorination of the terminal OH function, reaction with the sulfone building block, reduction of the phenylsulfonyl function, deprotection.

Result: When [(2E,6E)-3,7-dimethyl-8-[(tert.-butyldimethylsilyl)oxy]-2,6-octadienyl]phenylsulfone is used, (2(1')Z,5E,9E,13E,17E,21E,25E)-2-[2'-(2,5-dihydroxy-phenyl)ethylidene]-6,10,14,18,22,26-hexamethyl-27-hydroxy-5,9,13,17,21,25-heptaicosahexaenic acid is obtained.

Result: When [(2E,6E)-3,7-dimethyl-2,6-octadienyl]phenylsulfone is used, (2(1')Z,5E,9E,13E,17E,21E,25E)-2-[2'-(2,5-dihydroxyphenyl)ethylidene]-6,10,14,18,22,26-hexamethyl-5,9,13,17,21,25-heptaicosahexaenic acid is obtained.

For further chain extension, the reaction cycle described is again employed.

Example 32
Functionalization of the Terminal OH Group of Ganomycin A—Introduction of an Azide Function Methods: To a solution of 0.31 g (0.50 mmol) of (2(1')Z,5E,9E)-11-chloro-2-[2'-(2,5-bis[(tert.-butyldimethylsilyl)oxy]phenyl)ethylidene]-6,10-dimethyl-5,9-undecadienic acid methyl ester in 1.00 ml of dry DMF is added 36 mg (0.55 mmol) of sodium azide. The solution is heated up to 120° C. and stirred at this temperature for 6 hours. The cooled-down solution is poured onto 5 g of ice and extracted three times with 3 ml each of ether. The combined ether fractions are dried over magnesium sulfate, followed by distilling off the solvent under reduced pressure. The remaining residue is purified by column chromatography (mobile system heptane:ethyl acetate=10:1). The yield was 245 mg (0.39 mmol, 78%) of (2(1')Z,5E,9E)-1 1-azido-2-[2'-(2,5-bis[(tert.-butyidimethylsilyl)oxy]phenyl)ethylidene]-6,10-dimethyl-5,9-undecadienic acid methyl ester.

Result: Deprotection as described in Example 24 yields (2(1')Z,5E,9E)-11-azido-2-[2-(2,5-bishydroxyphenyl)ethylidene]-6,10-dimethyl-5,9-undecadienic acid.

Example 33
Functionalization of the Terminal OH Group of Ganomycin A—Introduction of a Fluorine Atom Methods: To a solution of 0.11 g (0.87 mmol) of dimethylaminotrimethylsilane in 2.5 ml of trichlorofluoromethane is added 0.14 ml (1.05 mmol) of diethylaminosulfur trifluoride (DAST) at −78° C. After 10 minutes of stirring at this temperature, the solution is warmed up to room temperature and subsequently cooled down again to 78° C. The addition of 301 mg (0.50 mmol) of (2(1')Z,5E,9E)-2-[2'-(2,5-bis[(tert.-butyidimethylsilyl)oxy]phenyl)ethylidene]-6,10-dimethyl-11-hydroxy-5,9-undecadienic acid methyl ester (preparation see Example 28) dissolved in 1.25 ml of trichlorofluoromethane is done by means of a syringe. After 45 minutes of stirring, the solution is warmed up to room temperature, poured onto 5 ml of ice water and extracted three times with 5 ml each of ether. The combined organic phases are washed with 10 ml each of saturated aqueous NaHCO₃ solution and with saturated aqueous NaCl solution, dried over MgSO₄ and concentrated under reduced pressure.

The remaining residue is purified by column chromatography (mobile system heptane:ethyl acetate=10:1). The yield was 127 mg (0.21 mmol, 42%) of (2(1')Z,5E,9E)-2-[2'-(2,5-bis[(tert.-butyldimethylsilyl)oxy]phenyl)ethylidene]-6,10-dimethyl-11-fluoro-5,9-undecadienic acid methyl ester.

Result: Deprotection as described in Example 23 yields (2(1')Z,5E,9E)-2-[2'-(2,5-bishydroxyphenyl)ethylidene]-6,10-dimethyl-11-fluoro-5,9-undecadienic acid.

Example 34
Functionalization of the Terminal OH Group of Ganomycin A—Oxidation to an Aldehyde Function Methods: To a suspension, stirred under argon, of 0.92 g (10.56 mmol) of activated manganese dioxide in 15 ml of petroleum ether is added dropwise 301 mg (0.50 mmol) of (2(1')Z,5E,9E)-2-[2'-(2,5-bis[(tert.-butyldimethylsilyl)-oxy]phenyl)ethylidene]-6,10-dimethyl-11-hydroxy-5,9-undecadienic acid methyl ester (preparation see Example 28) dissolved in 1.0 ml of petroleum ether. After 8 hours of intensive stirring, the solution is filtered through kieselguhr, the remaining residue is washed with ether, and the combined organic phases are dried over magnesium sulfate and concentrated under reduced pressure. Further purification is not necessary. The yield was 270 mg (0.45 mmol, 90%) of (2(1')Z,5E,9E)-2-[2'-(2,5-bis[(tert.-butyldimethylsilyl)oxy]phenyl)ethylidene]-10-formyl-6-methyl-5,9-undecadienic acid methyl ester.

Result: Deprotection as described in Example 24 yields (2(1')Z,5E,9E)-2-[2'-(2,5-bishydroxyphenyl)ethylidene]-10-formyl-6-methyl-5,9-undecadienic acid.

Example 35
Functionalization of the Terminal OH Group of Ganomycin A—Introduction of Two Fluorine Atoms Methods: To a solution of 0.11 g (0.87 mmol) of dimethylaminotrimethylsilane in 2.5 ml of trichlorofluoromethane is added 0.14 ml (1.05 mmol) of diethylaminosulfur trifluoride (DAST) at −78° C. After 10 minutes of stirring at this temperature, the solution is warmed up to room temperature and subsequently cooled down again to −78°. The addition of 300 mg (0.50 mmol) of (2(1')Z,5E,9E)-2-[2'-(2,5-bis[(tert.-butyldimethylsilyl)oxy]phenyl)ethylidene]-10-formyl-6-methyl -5,9-un-decadienic acid methyl ester (preparation see Example 32) dissolved in 1.25 ml of trichlorofluoromethane is done by means of a syringe. After 45 minutes of stirring, the solution is warmed up to room temperature, poured onto 5 ml of ice water and extracted three times with 5 ml each of ether. The combined organic phases are washed with 10 ml each of saturated aqueous NaHCO₃ solution and with saturated aqueous NaCl solution, dried over MgSO₄ and concentrated under reduced pressure.

The remaining residue is purified by column chromatography (mobile system heptane:ethyl acetate=10:1). The yield was 140 mg (0.23 mmol, 45%) of (2(1')Z,5E,9E)-2-[2'-(2,5-bis[(tert.-butydimethylsilyl)oxy]phenyl)ethylidene]-11,11-difluoro-6,10-dimethyl-5,9-undecadienic acid methyl ester.

Result: Deprotection as described in Example 24 yields (2(1')Z,5E,9E)-2-[2'-(2,5-bishydroxyphenyl)ethylidene]-11,11-difluoro-6,10-dimethyl-5,9-undecadienic acid.

Example 36
Functionalization of the Terminal OH Group of Ganomycin A—Etherification of the OH Function Methods: A solution of 301 mg (0.50 mmol) of (2(1')Z,5E,9E)-2-[2'-(2,5-bis[(tert.-butyldimethylsilyl)oxy]phenyl)ethylidene]-6,10-dimethyl-11-hydroxy-5,9-undecadienic acid methyl ester (preparation see Example 28) in 1.0 ml of DMF is slowly added at 0° C. under an argon atmosphere to a suspension of 20 mg (0.80 mmol) of NaH in 0.5 ml of DMF. The mixture is stirred at the stated temperature for 30 minutes and then warmed up to room temperature. Now, 0.82 mmol of the halide specified in Table 15 is added. The reaction mixture is stirred at room temperature for 36 hours, poured onto 10 ml of ice water and extracted three times with 5 ml each of ether. The combined organic phases are washed with 10 ml of saturated aqueous NaCl solution, dried over MgSO₄ and concentrated under reduced pressure. The remaining residue is purified by column chromatography (mobile system heptane:ethyl acetate=10:1).

TABLE 15

Reaction products and yields for different halides employed

| Halide | Yield | Product |
|---|---|---|
| benzyl bromide | 70% | (2(1')Z,5E,9E)-2-[2'-(2,5-bis[(tert.-butyldimethylsilyl)-oxy]phenyl)ethylidene]-6,10-dimethyl-11-phenyl-methoxy-5,9-undecadienic acid methyl ester |
| ethyl bromide | 74% | (2(1')Z,5E,9E)-2-[2'-(2,5-bis[(tert.-butyldimethylsilyl)-oxy]phenyl)ethylidene]-6,10-dimethyl-11-ethoxy-5,9-undecadienic acid methyl ester |
| methyl iodide | 80% | (2(1')Z,5E,9E)-2-[2'-(2,5-bis[(tert.-butyldimethylsilyl)-oxy]phenyl)ethylidene]-6,10-dimethyl-11-methoxy-5,9-undecadienic acid methyl ester |

Result: Deprotection as described in Example 24 yields 11-phenylmethoxy-, 11-ethoxy and 11-(methyl-2,3,4-tri-O-benzyl-6-deoxy-β-D-glucopyranos-6-yl)oxy-(2(1')Z,5E,9E)-2-[2'-(2,5-bishydroxyphenyl)ethylidene]-6,10-dimethyl-5,9-undecadienic acid.

Example 37
Functionalization of the Terminal OH Group of Ganomycin A—Introduction of an Amino Function Methods: To a solution of 157 mg (0.25 mmol) of (2(1')Z,5E,9E)-11-azido-2-[2'-(2,5-bis[(tert.-butyldimethylsilyl)oxy]phenyl)ethylidene]-6,10-dimethyl-5,9-undecadienic acid methyl ester in 2.5 ml of dry pyridine is added 0.13 g (0.50 mmol) of triphenylphosphine. After about 2 hours of stirring at room temperature, the reaction solution is mixed with 2.5 ml of acetaldehyde and stirred for another 12 hours at room temperature. The residue remaining after distilling off the solvent under reduced pressure is taken up in 5 ml of ether and washed twice with 2.5 ml each of 3% aqueous sodium hydrogensulfate solution and subsequently twice with 2.5 ml each of distilled water. After drying with magnesium sulfate, the solvent is distilled off under reduced pressure, and the remaining residue is purified by column chromatography (mobile system heptane:ethyl acetate=10:1). The yield was 212 mg (0.33 mmol, 66%) of (2(1')Z,5E,9E)-11-(N-acetylamino)-2-[2'-(2,5-bis[(tert.-butyldimethylsilyl)oxy]phenyl)ethylidene]-6,10-dimethyl-5,9-undecadienic acid methyl ester.

Result: Deprotection as described in Example 24 yields (2(1')Z,5E,9E)-11-(N-acetylamino)-2-[2'-(2,5-bishydroxyphenyl)ethylidene]-6,10-dimethyl-5,9-undecadienic acid.

Example 38
Reaction With Phthalic Anhydride

Methods: 500 mg (3.38 mmol) of phthalic anhydride is heated under reflux together with 301 mg (0.50 mmol) of (2(1')Z,5E,9E)-2-[2'-(2,5-bis[(tert.-butyidimethylsilyl)oxy] phenyl)ethylidene]-6,10-dimethyl-11-hydroxy-5,9-undecadienic acid methyl ester (preparation see Example 28) in 5 ml of toluene for two hours. The cooled-down solution is washed with 3 ml each of saturated aqueous $NaHCO_3$ solution and with saturated aqueous NaCl solution, dried over $MgSO_4$ and concentrated under reduced pressure. The remaining residue is purified by column chromatography (mobile system heptane:ethyl acetate=10:1). The yield was 75 mg (0.10 mmol, 20%) of the phthalic acid monoester in addition to 40 mg (0.03 mmol, 12%) of the phthalic acid diester.

Result: The hydrophilicity of the compounds of formula 1 is considerably enhanced.

Example 39
Oxidation of the Hydroquinones

Methods: With stirring at room temperature, 0.01 mmol of ganomycin B in 10 ml of methylene chloride is reacted with 0.02 mmol of cerium(IV) ammonium nitrate (ammonium hexanitratocerate(IV)=$(NH_4)_2Ce(NO_3)_6$) for 3 hours, the mixture is added to 20 ml of water, shaken in a separating funnel, the organic phase is separated off, and the solvent removed.

Result: Oxidation of the hydroquinones broadens the possible applications of the active substances of formula 1.

Example 40
Esterification With the Gyrase Inhibitor Ofloxacin

To a solution of 55 mg (0.15 mmol) of ofloxacin in 0.5 ml of dry pyridine is added slowly at 0° C. under an inert gas atmosphere 108 mg (0.38 mmol) of trifluoromethane-sulfonic acid anhydride using a syringe. The solution is warmed up to room temperature and stirred for two hours. This is followed by the addition of 905 mg (1.50 mmol) of (2(1')Z,5E,9E)-2-[2'-(2,5-bis[(tert.-butyldimethylsilyl)-oxy] phenyl)ethylidene]-6,10-dimethyl-11-hydroxy-5,9-undecadienic acid methyl ester, the synthesis of which was described in Example 28, dissolved in 0.5 ml of dry pyridine. The reaction solution is stirred at room temperature for another 2 hours, then poured onto 5 ml of ice water and extracted three times with 5 ml each of ether. The combined organic phases are washed with 5 ml each of 3% aqueous $NaHSO_4$ solution and with distilled water, dried over $MgSO_4$ and concentrated under reduced pressure. Separation of the obtained residue by HPLC (mobile system heptane:ethyl acetate=5:1) yields 47 mg (0.05 mmol, 33%) of the ofloxacin ester of formula 12 and 403 mg (0.67 mmol, 44%, based on the mass employed) of the unreacted (2(1') Z,5E,9E)-2-[2'-(2,5-bis[(tert.-butyl-dimethylsilyi)oxy] phenyl)ethylidene]-6,10-dimethyl-11-hydroxy-5,9-undecadienic acid methyl ester.

Example 41
Esterification With Penicillin G

To a solution, cooled down to −20° C., of 100 mg (0.30 mmol) of penicillin G and 235 mg (0.39 mmol) of (2(1')Z, 5E,9E)-2-[2'-(2,5-bis[(tert.-butyidimethylsilyl)-oxy]phenyl) ethylidene]-6,10-dimethyl-11-hydroxy-5,9-undecadienic acid methyl ester, the synthesis of which was described in Example 28, in 1.50 ml of dry dichloromethane is added under an inert gas atmosphere 0.13 ml (1.64 mmol) of pyridine and 72 mg (0.39 mmol) of cyanuric chloride. After two hours of stirring at the stated temperature, 5 ml of dichloromethane and 5 ml of 1.0 M aqueous sulfuric acid are added, the organic phase is separated off, and the aqueous phase is extracted two more times with 5 ml each of dichloromethane. The combined organic phases are washed with 5 ml each of saturated aqueous $NaHCO_3$ solution and saturated aqueous NaCl solution, dried over $MgSO_4$ and concentrated under reduced pressure. The purification of the obtained residue by HPLC (mobile system heptane:ethyl acetate=5:1) yields 47 mg (0.13 mmol, 43%) of the "penicillin G" ester of formula 10.

Example 42
Active Substances of General Formula 1 With a Carbohydrate Residue as Substituent R5

Methods: A solution of 301 mg (0.50 mmol) of (2(1')Z, 5E,9E)-2-[2'-(2,5-bis[(tert.-butyldimethylsilyl)oxy]phenyl) ethylidene]-6,10-dimethyl-11-hydroxy-5,9-undecadienic acid methyl ester (preparation according to Example 28) in 1.0 ml of DMF is slowly added at 0° C. under an argon atmosphere to a suspension of 20 mg (0.80 mmol) of NaH in 0.5 ml of DMF. The mixture is stirred for 30 minutes at the stated temperature and then warmed up to room temperature. Now, 0.82 mmol of methyl-2,3,4-tri-O-benzyl-6-deoxy-6-iodo-β-D-glucopyranoside is added. The reaction mixture is stirred at room temperature for 36 hours, poured onto 10 ml of ice water and extracted three times with 5 ml each of ether. The combined organic phases are washed with 10 ml of saturated aqueous NaCl solution, dried over $MgSO_4$ and concentrated under reduced pressure. The remaining residue is purified by column chromatography (mobile system heptane:ethyl acetate=10:1).

Result: (2(1')Z,5E,9E)-2-[2'-(2,5-bis[(tert.-butyldimethylsilyl)oxy]phenyl)ethylidene]-6,10-dimethyl-11-[(methyl-2,3,4-tri-O-benzyl-6-deoxy-β-D-glucopyranos-6-yl)oxy]-5,9-undecadienic acid in a yield of 51%. Deprotection is effected as described in Example 24 to yield 11-(methyl-2,3,4-tri-O-benzyl-6-deoxy-β-D-glucopyranos-6-yl)oxy]-(2(1')Z,5E,9E)-2-[2'-(2,5-bishydroxyphenyl) ethylidene]-6,10-dimethyl-5,9-undecadienic acid.

Example 43
Esterification With Fusidinic Acid

Methods: The compounds of the formula with R5=$CH_2OH$ is reacted in a 1.35-fold equimolar ratio with fusidinic acid (20 mM) in an organic solvent under the influence of a lipase (2.5%; obtained from, e.g., Candida rugosa or Mucor miehei, Sigma Aldrich Chemie GmbH) for 6 h at 35° C. To support the reaction rate, the reaction solutions are agitated at 100 rpm. The yield of condensation products is 40%.

Result: Esterification with fusidinic acid causes an increase of surface activity and an enhancement of the lipophilic properties.

Example 44
Preparation of Novel Antimicrobially Active Substances by Condensation of an Active Substance of General Formula 1, With R1–R3=H, R4=COOH and R5=$CH_3$, With 6-Aminopenicillanic Acid by Means of Biotransformation Methods: The compound of formula 1 with R1–R3=H, R4=COOH and R5=$CH_3$ is reacted in an equimolar ratio with 6-aminopenicillanic acid (20 mM) in 0.1 M sodium phosphate buffer (pH 6.0) under the influence of a penicillin acylase (0.50%; obtained from, e.g., *E. coli*, Sigma Aldrich Chemie GmbH) for 4 h at 35° C. To support the reaction rate, the reaction solutions are agitated at 100 rpm.

Result: The yield of condensation products was 53%.

Example 45
Preparation of Novel Antimicrobially Active Substances by Condensation of the Active Substances of General Formula 1, With R1–R3=H, R4=COOH and R5=CH$_3$, With 7-Aminocephalosporinic Acid by Means of Biotransformation Methods: The compound of formula 1 with R1–R3=H, R4=COOH and R5=CH$_3$ is reacted in an equimolar ratio with 7-aminocephalosporinic acid (20 mM) in 0.1 M sodium phosphate buffer (pH 7.0) under the influence of an acylase (0.50%; obtained from Bacillus megaterium according to Toyo Jozo Company, 1974, British Patent 1,347,665) for 2 h at 37° C. To support the reaction rate, the reaction solutions are agitated at 100 rpm.

Result: The yield of condensation products was 46%.

Example 46
Preparation of Novel Antimicrobially Active Substances by Condensation of the Active Substances of General Formula 1, With R1–R3=H, R4=COOH and R5=CH$_3$, With 7-Aminodeacetoxycephalosporinic Acid by Means of Biotransformation The compound of formula 1 with R1–R3=H, R4=COOH and R5=CH$_3$ is reacted in an equimolar ratio with 7-aminodeacetoxycephalosporinic acid (40 mM) in 0.1 M sodium phosphate buffer (pH 6.0) under the influence of an acylase (0.5%; obtained from, e.g., E. coli) for 100 min at 37° C. To support the reaction rate, the reaction solutions are agitated at 100 rpm.

Result: The yield of condensation products was 55% and 60%.

Example 47
Preparation of Novel Antimicrobially Active Substances by Condensation of the Active Substances of General Formula 1, With R1–R3=H, R4=COOCH$_3$ and R5=CH$_3$, With 7-Aminocephalosporinic Acid by Means of Biotransformation The preparation is effected in accordance with Example 46. The yield is about 63%.

Example 48
Proof of the Free-radical Scavenging Property of the Extracts Using Chemiluminescence The proof was established as follows:

A: 30 ml of human blood was preincubated with 170 ml of PBS+luminol (0.33 mM final) at 37° C. for 20 min.

B: 30 μl of human blood was preincubated with 170 ml of PBS+luminol (0.33 mM final) and 20 ml of substance dilution at 37° C. for 20 min.

To A was pipetted 20 μl of a 1:100 dilution of the extract of Example 11 and 20 μl of zymosan (10 mg/ml).

To B was pipetted 20 μl of zymosan (10 mg/ml).

As a control, PBS was used instead of zymosan as a stimulator with and without substance in charges A and B. After intensive mixing, the kinetics of the luminescence were measured over 60 min. The examinations were performed on two different days with blood from two different blood donors.

Result: The extracts clearly inhibit luminol-induced and spontaneous oxygen free-radical release or scavenge the released free radicals.

Example 49
Inhibition of Neutral Endopeptidase

Methods: The proof of specific inhibition of neutral endopeptidase was established according to Meizig et al., Pharmazie 51 (1996) 501–503.

Result: The extract obtained from the fruit body using 80% alcohol achieves an inhibition by 68% at a concentration of 100 μg/ml, and by 84% at 200 μg/ml.

With the corresponding ethanolic extract of the cultured mycelium, the activity of the enzyme was inhibited by 70% already at a concentration of 50 μg/ml.

The aqueous extracts from the fruit body and mycelium are also effective. Upon incubation with 50 μg/ml of the cold-water extract, an inhibition of the enzyme activity by 65% was found.

Example 50
Use of the Extracts for Inhibiting the Activity of Proteases

Proteases are involved in numerous posttranslational processes of functional regulation of the macroorganism. Upon inhibition of the proteases, a wide variety of pharmacological effects are to be expected. The proof of enzyme inhibition by aqueous and ethanolic extracts according to Examples 15 and 16 was established in an exemplary manner with the angiotensin-converting enzyme according to Melzig et al., Pharmazie 51 (1996), 501–503.

Result: The aqueous and ethanolic extracts exhibit inhibition of the angiotensin-converting enzyme at concentrations of 100–200 μg/ml.

Example 51
Influence on Serum-mediated Lipopolysaccharide Binding

Methods: The test was performed according to Grunwald (CD-14 als Rezeptor für Endotoxin: in vitro-Untersuchungen zu Bindungsmodalitäten von LPS und zur Beeinflussung der Expression. Dissertation Ernst-Moritz-Arndt-Universität Greifswald 1993). For the tests, cell lines from ovaries of Chinese hamsters were used which express the CD-14 receptor after transfection of the CD-14 gene. The lipopolysaccharide was labeled with FITC so that the binding to the receptor could be determined by measuring the fluorescence intensity.

Result: Ethanolic extracts from fruit bodies according to Example 2 and mycelium according to Example 15 in concentrations of between 0.1 and 0.20% achieved an inhibition of serum-mediated lipopolysaccharide binding by 40–60%; similarly, the active substance according to Examples 22 and 23 causes inhibition of the lipopolysaccharide binding.

Lipopolysaccharides are released from the cell wall of Gram-negative bacteria upon infection therewith. After binding to the lipopolysaccharide-binding protein, they can induce macrophages and mononuclear cells to release endogenous mediators and thus cause fever, changes in the white blood picture, and abnormal distension of the vessels in the body periphery. In the worst case, a septic shock can result from the lipopolysaccharide binding.

Therefore, extracts and active substances isolated therefrom which, on the one hand, inhibit the growth of the invaded bacteria due to their antimicrobial properties and, on the other hand, reduce the binding of the released lipopolysaccharides have many advantages for application as a medicament.

Example 52
Use of Biologically Active Extracts From Fungi of the Genus Ganoderma as Preservatives for Technical Purposes Methods: A hot-water extract from fruit bodies of G. pfeifferi was added at a concentration of 2% to a surfactant solution having the following composition: alkylbenzenesulfonate 8.0; alkanesulfonate 8.1; alkyl polyglycol ether 3.1; sodium polyphosphate 1.0; perfume oil 0.005; water ad 100. The sample and a corresponding control are contaminated with *S. aureus*. After 24 h has elapsed, 1 ml was withdrawn and added to 10 ml of a neutralization mixture of casein peptide/soybean/broth with 3% Tween 80, 0.3% lecithin and 0.1% cysteine. Subsequently, the germ number was determined on casein peptone/soybean/agar (Oxoid, Unipath Ltd., Basingstoke, Hampshire, GB).

Result: While the germ number in the non-preserved controls was $3.1 \times 10^8$, the preserved samples remained germ-free.

Example 53
Application as a Vitalizing and Germ-reducing Additive for Pharmaceutical and Cosmetic Formulations Which Protects From Free Radicals Methods: The antimicrobial activity was proven in an agar diffusion test according to Example 1, and the preserving property was proven in a preservation loading test with a water-in-oil skin care cream inoculated with *S. aureus* at a titer of $1:10^6$.

The proof of the free-radical scavenging function was established in accordance with Example 48.

Result: The alcoholic extracts had antibacterial activity, and no germ growth was detected in the samples protected by the alcoholic extracts according to Example 17.

The addition of hydroquinones prevents oxidative decompositions and causes protection from skin-damaging free-radical formers due to its free-radical scavenging properties.

In addition, the Ganoderma extracts have an anti-inflammatory effect. The combination of these properties offers good conditions for application in the cosmetics industry.

Example 54
Use of Alcoholic and Aqueous Extracts From the Mycelium and Fruit Bodies of *G. pfeifferi* as Vitalizing, Pain-relieving and Germ-reducing Additives for Foods Methods: The protection of cells from toxic radicals as proven according to Example 48 may also be considered important in terms of physiology of nutrition in the supplementing of foods with extracts from *G. pfeifferi*. Alimentary supplementation is also performed for other cofactors of antioxidative systems, such as vitamins C and E and trace elements for the detoxification of oxygen radicals. This effect specific of extracts from *G. pfeifferi* is very advantageously complemented by the previously known immunostimulation also established for other fungi of the genus Ganoderma. On the other hand, the specific inhibiting effect of the extracts from *G. pfeifferi* on neutral endopeptidase can be utilized for pain relief because they interfere with the degradation of neuropeptides and endorphins acting on the opiate receptors due to inhibition of an encephalinase.

Due to the strong inhibition of neutral endopeptidase, inhibition of the adsorption of viruses to the cellular surface and thus an antiviral effect can be additionally expected.

Result: The combination of free-radical scavenging properties, immunostimulant activity, pain-relieving activity and antimicrobial properties provides very favorable conditions for application as a food supplement.

Example 55
Use as a Health Care Agent and Food Supplement

Methods: Aqueous and alcoholic extracts from fungi of the genus Ganoderma inhibit the cholesterol accumulation in cultured human aortic intimal cells and the proliferation of the cells, providing protection from arteriosclerosis. The inhibition of neutral endopeptidase and of the angiotensin-converting enzyme interferes in functions of the acid metabolism which are organized in a cascade-like manner.

According to Melzig et al., Pharmazie 51 (1996), 501–503, the inhibition of neutral endopeptidase as established in Example 49 causes an enhancement of the renal sodium excretion and thus a reduction in blood pressure. According to Gräfe (Biochemie der Antibiotika, Spektrum Akademischer Verlag, Heidelberg, Berlin, New York, 1992), the inhibition of the angiotensin-converting enzyme as established in Example 50 also results in a reduction in blood pressure.

Result: Since many patients exhibiting a metabolic syndrome combine an increased cholesterol level with an increased blood pressure, the known effects of fungi of the genus Ganoderma are very advantageously complemented by the blood-pressure reducing effect in *G. pfeifferi*.

Ethanolic extracts from fruit bodies according to Example 2 and mycelium according to Example 7 in concentrations of between 0.1 and 0.2% achieved an inhibition Of serum-mediated lipopolysaccharide binding by 40–60%; similarly, the active substance according to Example 22 causes inhibition of the lipopolysaccharide binding.

Lipopolysaccharides are released from the cell wall of Gram-negative bacteria upon infection therewith. After binding to the lipopolysaccharide-binding protein, they can induce macrophages and mononuclear cells to release endogenous mediators and thus cause fever, changes in the white blood picture, and abnormal distension of the vessels in the body periphery. In the worst case, a septic shock can result from the lipopolysaccharide binding.

Therefore, extracts and active substances isolated therefrom which, on the one hand, inhibit the growth of the invaded bacteria due to their antimicrobial properties and, on the other hand, reduce the binding of the released lipopolysaccharides have many advantages for application as a medicament.

Example 56
Application in Human and Veterinary Medicine, Especially in the Control of Infections as a Sole Active Substance and in the Form of Combination Preparations Methods: Extracts according to Example 9 in a concentration of 2 mg/l were dropped onto standardized test plates for the resistance assay for the commercially available antibiotics amicazin, trimethroprim and fusidinic acid (Sensi-Disk Antibiotics Test Plates, Becton Dickinson Microbiology Systems, Cockeysville, USA). The antibacterial activity was determined according to Example 1 on multiresistant coagulase-negative staphylococci isolated from patient material.

Result: The extracts according to the invention, active substances isolated therefrom and combinations with conventional antibiotics are effective against staphylococci isolated from patient material (Table 16).

TABLE 16

Antibacterial activity of extracts, active substances isolated therefrom and combinations

| | Inhibition halo (mm) | | |
|---|---|---|---|
| | *S. epidermidis* 473 | *S. epidermidis* 125 | *S. epidermidis* 847 |
| Extract according to Example 9 | 10 | 10 | 12 |
| Ganomycin B | 20 | 16 | 16 |
| Extract according to Example 9 + amicazin | 18 | 14 | 18 |

TABLE 16-continued

Antibacterial activity of extracts, active substances isolated therefrom and combinations

| | Inhibition halo (mm) | | |
|---|---|---|---|
| | S. epidermidis 473 | S. epidermidis 125 | S. epidermidis 847 |
| Extract according to Example 9 + trimethroprim | 40 | 30 | 34 |
| Extract according to Example 9 + fusidinic acid | 34 | 28 | 30 |

Example 57
Use of the Substituted Hydroquinones of General Formula 1 in Human and Veterinary Medicine as an Agent Having Antimicrobial Activity, Especially for Multiresistant Gram-positive Germs Methods: Active substances of general formula 1 with $R_1$–$R_3$=H, $R_4$=COOH, $R_5$=$CH_3$ were examined for activity against pathogens of Gram-positive infections in an agar diffusion test according to Example 1.

Result: Both methicillin-sensitive *Staph. aureus* strains and methicillin-resistant strains, such as the North-German Epidemy Strain, are inhibited by ganomycin B. Multiresistant *S. epidermidis* and *S. haemolyticus* strains isolated from patient material are also inhibited. Activity against resistant enterococci was also observed (Table 17).

TABLE 17

Antibacterial activity against pathogens of Gram-positive infections

| Pathogen | Inhibition halo (mm) |
|---|---|
| S. aureus ATCC 6538 | 30 |
| S. aureus ATCC 25923 | 25 |
| S. aureus ATCC 29213 | 22 |
| S. aureus reference strain "North-German Strain" (Smith Kline Beecham) | 16 |
| S. aureus (MRSA strains isolated from patient material) | 10–16 |
| S. epidermidis (multiresistant strains isolated from patient material) | 16–20 |
| S. haemolyticus (multiresistant strains isolated from patient material) | 12–16 |
| Enterococci (multiresistant strains isolated from patient material) | 10–14 |

Due to the strong inhibition of neutral endopeptidase, inhibition of the adsorption of viruses to the cellular surface and thus an antiviral effect can be additionally expected.

Example 58
Use as an Agent Against Fish-pathogenic Bacteria and in Fish Breeding Methods: Fish bacterioses pose a special economic and ecologically relevant problem. The examinations were made with Gram-negative bacteria which cause fish diseases such as red mouth epidemic or the red plague. The growth of the bacteria supplied by the Staatlicher Fischseuchenbekampfungsdienst Niedersachsen and by the Fischgesundheitsdienst was effected on trypticase-soybean agar (Sigma Chemical Co., St. Louis, USA). The examination of the extracts from the fruit body and active substances was performed in an agar diffusion test.

Result: Especially against the Aeromonas species, an antibacterial activity was found (Table 18). Since the extracts according to the invention are natural substances, a good ecological tolerance is to be expected.

TABLE 18

Application in fish breeding

| | Diameter of inhibition halo (mm) | | | |
|---|---|---|---|---|
| Extract or active substance | Aeromonas salmonicida subsp. salmonicida 67 A 1 | Aeromonas hydrophila DSM 30019 | Vibrio anguillarum ATCC 1188 | Yersinia ruckeri F 531/82 |
| Dichloromethane extract | 10 | 12 | — | — |
| Ethanolic extract | 10 | 10 | — | — |
| Cold-water extract | 9 | 8 | — | — |
| Hot-water extract | 13 | 14 | 9 | 10 |
| Ganomycin A | 10 | 15 | 10 | — |
| Ganomycin B | 12 | 17 | 26 | — |

Example 59
Use as Free-radical Scavengers

Methods: The free-radical scavenging function of the active substances of formula 1, ganomycin A and ganomycin B, broadens the possibilities of medicinal use. The proof was established as in the examination of the extracts according to Example 48.

Result: The ganomycins A and B inhibit luminol-induced and spontaneous oxygen free-radical release at a concentration of 10 μg/ml.

The combination of free-radical scavenging properties and antimicrobial properties offers very favorable conditions for application.

What is claimed is:

1. A Ganoderma extract comprising a solvent extract of *Ganoderma pfeifferi* DSM 13239, the extract having biological activity, wherein the biological activity is antimicrobial activity and/or natural-endopeptidase inhibiting activity and/or angiotensin-converting-enzyme inhibiting activity and/or inhibiting serum-mediated-binding-of-lipopolysaccharide inhibiting activity.

2. The Ganoderma extract of claim 1, obtained from the fruit body of *Ganoderma pfeifferi* DSM 13239.

3. The Ganoderma extract of claim 3, wherein *Ganoderma pfeifferi* DSM 13239 is grown on wood substrates in mushroom farms.

4. The Ganoderma extract of claim 3, wherein the wood substrates contain cellulose-degrading enzymes.

5. The Ganoderma extract of claim 1, obtained from the mycelium of *Ganoderma pfeifferi* DSM 13239 grown in medium in a fermenter.

6. The Ganoderma extract of claim 5, wherein the medium is a liquid containing ammonium succinate.

7. The Ganoderma extract of claim 5, wherein *Ganoderma pfeifferi* DSM 13239 is grown in a liquid culture medium with carbohydrate sources, with observance of a lighting and shaking regimen.

8. The Ganoderma extract of claim 5, wherein *Ganoderma pfeifferi* DSM 13239 is grown in a liquid malt culture medium with carbohydrate sources having a content of malt extract of from 20 to 40 g/1000 l and an initial pH of 4.5–7.5, with observance of a lighting and shaking regimen.

9. The Ganoderma extract of claim 8, wherein the malt culture medium contains wood extract, alone, or in combination with cellulose-degrading enzymes.

10. The Ganoderma extract of claim 9, wherein the wood extract is a decoction from beech.

11. The Ganoderma extract of claim 1, wherein the solvent is a lipophilic solvent.

12. The Ganoderma extract of claim 1, wherein the solvent is dichloromethane.

13. The Ganoderma extract of claim 1, wherein the solvent is a monohydric alcohol.

14. The Ganoderma extract of claim 1, wherein the solvent is water and extraction is effected stepwise with increasing water temperature.

15. The Ganoderma extract of claim 14, wherein the water temperature is 10 to 80° C.

16. The Ganoderma extract of claim 1, wherein the extract is ethyl acetate.

17. The Ganoderma extract of claim 1, obtained by extraction with a lipophilic solvent followed by extraction with ethyl acetate from the lipophilic-solvent extract.

18. The Ganoderma extract of claim 1, obtained by extraction with a lipophilic solvent followed by extraction with a monohydric alcohol from the lipophilic-solvent extract.

19. The Ganoderma extract of claim 1, obtained by extraction with a lipophilic solvent, followed by extraction with a monohydric alcohol from the lipophilic-solvent extract, followed by extraction with ethyl acetate from the monohydric-alcohol-solvent extract, and followed by purification the ethyl-acetate-solvent extract monohydric alcohol on silica gel using a gradient.

* * * * *